United States Patent
Baker et al.

(10) Patent No.: US 6,848,894 B2
(45) Date of Patent: Feb. 1, 2005

(54) ABSORBENT ARTICLE, METHOD AND APPARATUS FOR PREPARING SAME

(75) Inventors: Andrew Baker, Lawrenceville, GA (US); Doug Frederisy, Alpharetta, GA (US)

(73) Assignee: Paragon Trade Brands, Inc., Norcross, GA (US)

( * ) Notice: Subject to any disclaimer, the term of this patent is extended or adjusted under 35 U.S.C. 154(b) by 159 days.

(21) Appl. No.: 09/793,679

(22) Filed: Feb. 27, 2001

(65) Prior Publication Data

US 2002/0169434 A1 Nov. 14, 2002

(51) Int. Cl.$^7$ ................................................. B27N 3/04
(52) U.S. Cl. ........................ 425/81.1; 425/80.1; 264/112; 264/121
(58) Field of Search ........................ 425/80.1, 81.1, 425/82.1, 83.1; 264/112, 121, 517

(56) References Cited

U.S. PATENT DOCUMENTS

| | | | |
|---|---|---|---|
| 2,912,723 A | * | 11/1959 | Roberts ..................... 425/83.1 |
| 3,501,813 A | | 3/1970 | Lee et al. |
| 3,518,726 A | | 7/1970 | Banks |
| 3,598,680 A | | 8/1971 | Lee |
| 3,939,240 A | | 2/1976 | Savich |
| 3,973,291 A | | 8/1976 | Kolbach |
| 3,975,222 A | | 8/1976 | Mesek |
| 3,994,047 A | | 11/1976 | Lee et al. |
| 4,016,628 A | | 4/1977 | Kolbach |
| 4,223,677 A | | 9/1980 | Anderson |
| 4,388,056 A | | 6/1983 | Lee et al. |
| 5,098,423 A | | 3/1992 | Pieniak et al. |
| 5,447,677 A | * | 9/1995 | Griffoul et al. ............. 264/510 |
| 5,466,513 A | | 11/1995 | Wanek et al. |
| 5,637,165 A | | 6/1997 | Chen |
| 5,788,684 A | | 8/1998 | Abuto et al. |
| 5,873,963 A | | 2/1999 | Trombetta et al. |
| 5,891,120 A | | 4/1999 | Chmielewski |
| 5,983,457 A | | 11/1999 | Toney et al. |
| 6,001,911 A | | 12/1999 | Ishizaki et al. |
| 6,056,854 A | | 5/2000 | Woodrum |
| 6,068,620 A | | 5/2000 | Chmielewski et al. |
| 6,273,978 B1 | | 8/2001 | Tai |

* cited by examiner

*Primary Examiner*—James P. Mackey
*Assistant Examiner*—Donald Heckenberg
(74) *Attorney, Agent, or Firm*—Hunton & Williams llp

(57) ABSTRACT

An apparatus and a method for preparing an absorbent article is disclosed. The apparatus has at least two forming surfaces which differ in terms of air permeability to allow the selective placement of fibrous material. The forming surface comprises a perforated forming screen. The forming screen has multiple zones with different amounts of open area through which air may pass. Particles carried in the air which flows through the open area are deposited on different zones of the forming screen resulting in different basis weights corresponding to the different air permeabilities. The apparatus and method thus provide an article having optimal zoned absorbency in a cost-effective manner.

38 Claims, 20 Drawing Sheets

ABSORBENT ARTICLE, METHOD AND APPARATUS FOR PREPARING SAME

FIELD OF THE INVENTION

The present invention relates generally to an apparatus and method for preparing an absorbent article, and a novel absorbent article. In particular, the invention relates to an apparatus which uses varying air flow to selectively place particles in an absorbent article to provide optimal absorbency in a cost-effective manner.

BACKGROUND OF THE INVENTION

Traditionally, disposable absorbent garments such as infant diapers and training pants, adult incontinent products, and other such products are constructed with a moisture-impervious outer backing sheet, a moisture-pervious body contacting inner lining sheet, and a moisture-absorbent core sandwiched between the liner and backing sheets.

Much effort has been expended to develop cost-effective absorbent cores which display optimal liquid absorbency and retention. In many applications, it is desirable to form an absorbent article having a zoned absorbency profile where different predetermined regions have different weights of particles per unit area, and, therefore, different absorbencies.

In the general practice of forming fibrous materials as absorbent articles, it has become a practice to utilize a fibrous sheet of cellulosic or other suitable fibers which is fiberized in a conventional fiberizer or other device to form discreet fibers which then are entrained in an air stream or airflow and directed to a forming surface whereon the fibers are deposited to form a pad of fluff, i.e. a non-woven mat of randomly arrayed fibers containing substantial interstitial void space and being highly compressible in character.

The forming surface utilized in such a system typically is constructed as a wire or screen grid and typically employs pneumatic flow means such as vacuum suction apparatus to define a differential pressure zone on the forming surface and impose a pressure differential thereon whereby the air in the air entrained fiber stream is passed through the openings or perforations in the screened grid of the forming surface. The use of vacuum suction to draw the air entrained fiber stream to the forming surface, with the passage of the air component through the forming surface, is highly efficient and lends itself to high speed commercial operations.

In the prior practice of forming laid fibrous articles, various means have been provided in the art for providing the fibrous article with gradations or variations in basis weight across the surface thereof. Such gradations can, for example, enhance the efficiency of the fibrous article in end usages such as disposable diapers and sanitary napkins. Various approaches, thus, have been attempted for producing gradations of basis weight.

For example, U.S. Pat. No. 4,388,056 to Lee et al. discloses an apparatus for continuously forming an air-laid fibrous web, comprising a laydown drum having a circumferentially segmented annular-shaped plenum comprising a multiplicity of circumferentially spaced transverse plenum segments, and a partially masked foraminous laydown surface having oppositely contoured, cyclically undulating side edges defining cyclically circumferentially spaced relatively wide masked and relatively narrow masked transverse areas of the surface, which together define the radially outward facing boundary of the plenum. Constant differential pressure means are employed for drawing air through the foraminous laydown surface and the plenum from an air-entrained-fiber deposition chute as the drum is rotated. The specific improvement of the invention comprises stationary adjustable air flow modulating means (shutter plates) disposed adjacent the radially inwardly disposed boundary of an arcuate portion of the plenum circumferentially spanning a plurality of the transverse plenum segments. In such manner, the pressure across the relatively widely masked transverse sections of the laydown surface can be adjusted without substantially affecting the pressure across the relatively narrowly masked transverse sections of the laydown surface.

This apparatus purportedly permits the formation of a fibrous web severable into uniform, contoured articles, such as fibrous absorbent cores for disposable diapers, having relatively thick, narrow absorbent crotch areas, and relatively thin waistband regions, without stepwise basis weight gradients. Thus, the areas of the foraminous laydown surface (screen) having the largest pressure differential across them (i.e., the narrow areas) experience greater fiber buildups or accumulations than the areas of the screen having lower pressure differentials across them (i.e., the wide areas), the narrow areas corresponding to the crotch regions of the web articles and the large areas corresponding to the waistband regions thereof.

Although the apparatus disclosed in the '056 patent is said to provide a smooth basis weight gradation in the machine direction (i.e., longitudinally) in the fibrous articles formed thereon, as noted particularly with reference to FIGS. 7 and 8 of this patent, the basis weight gradation of the fibrous article is both longitudinally and laterally symmetrical in distribution. Accordingly, the greatest basis weight occurs in a circular shaped region centered at the crotch with the basis weight uniformly radially decreasing therefrom, such that lines of nominally equal basis weights describe concentric circles radiating outwardly from such central region of highest basis weight. This design provides a high basis weight in the frontal crotch region. However, for reasons of liquid retention, it is said to be more advantageous to provide a longitudinally extending central region of high basis weight relative to the longitudinal peripheral margins, and further to provide a higher basis weight in the front panel of the fibrous article relative to its rear panel (the front and rear panels being considered here as the demarcated opposed symmetrical portions produced when the fibrous article is folded along a lateral fold line midway along its longitudinal extent). In comparison to these optimal basis weight characteristics of the fibrous web article, the fibrous articles produced by the apparatus of the Lee, et al. patent are seen to be deficient, particularly in the steady decline of such article's basis weight along the full longitudinal dimension of the front and rear panels, from a point centered at the crotch region of the article.

U.S. Pat. No. 3,939,240 to P. P. Savich discloses a method of dry forming fibrous pads by means of a condenser roll having three-dimensional cavities circumferentially disposed about the periphery thereof. The cavities each have foraminous bottom and side surfaces, with the surface area of the cavity being greater than the surface area of the opening into the cavity. Vacuum is applied through the foraminous surfaces of each cavity to pull the air component of a fibers/air suspension through the foraminous surfaces, thereby depositing the fibers carried in the air suspension onto the cavity surfaces. A transfer conveyor is proximately disposed to the cavity opening at its discharge position and vacuum also is supplied through the transfer conveyor, to transfer the fibrous layer from the cavity onto the conveyor.

The fibers deposited on the transfer conveyor are confined to an area substantially equal to the surface area of the cavity opening, so that the fibers are consolidated as they are transferred from the cavity onto the conveyor, forming fibrous pads having a greater basis weight than the basis weight of the fibrous layers formed in the cavities. This patent, in addition to embodiments disclosing the formation of discrete fibrous pads unassociated with any fibrous web, discloses an embodiment in which the outer periphery of the forming roll surrounding each cavity is also foraminous. In such manner, the fibrous pads formed from the fibrous layers within each cavity will be integrally joined with fibrous web sections of a lower basis weight.

U.S. Pat. No. 4,223,677 to J. E. Anderson discloses an absorbent fibrous structure which includes intermingled absorbent fibers of a varying length up to about 6.35 millimeters. The fibers are disposed in different classified layers having differing weighted average fiber length in each of the layers, with the weighted average fiber length decreasing from layer to layer in a direction from one outer surface to the opposite outer surface. The separate layers of the absorbent pad are not disclosed as having any varying weight within the respective layers, so that the basis weight therefore is constant along the longitudinal and transverse dimensions of the pad.

An apparatus for forming fibrous pads is disclosed in U.S. Pat. No. 3,973,291, to C. G. Kolbach, comprising a pad assembly having spaced three-dimensional pad-receiving compartments, separated by air-impermeable regions. The pad-receiving compartments are defined by lower air-permeable surfaces and air-impermeable side walls extending outwardly therefrom. The side wall sections of each compartment are movable relative to the lower air-permeable surface to assist in releasing formed pads from the compartments.

In column 8, lines 41 et seq, it is alleged that the patentee has discovered that formation of a profiled fibrous pad, i.e., one with a varying basis weight, "cannot be controlled within close tolerances by establishing a different amount of open area through which air can be drawn by a vacuum box through different predetermined regions underlying the different predetermined sections of the pad-receiving compartment in which different weights of fibers per unit area are to be deposited." Based on this discovery, it is contended that "the only effective means for establishing different weights of fiber per unit area in different predetermined regions of a fibrous pad, while maintaining close tolerances, is to completely form each predetermined region with a specific weight of fibers per unit area therein substantially independently of the formation of every other predetermined region having a different weight of fibers per unit area therein." The disclosed method thus involves completely masking off a source of vacuum to all sections of each pad-receiving compartment except the section in which region a fibrous pad having a particular weight of fibers per unit area is to be formed. After this region has been completely formed, the vacuum source underlying the formed region is completely masked to the passage of air, and a second section of each pad-receiving compartment is exposed to vacuum to form a predetermined region on the pad having a different weight of fibers per unit area therein. Thus, the patentee discloses a serial masking-unmasking sequence to provide the finished article.

U.S. Pat. No. 3,501,813 to C. A. Lee et al. discloses a method and apparatus for forming a single integral web of air-laid fibrous material with non-uniform cross-sectional thickness. The disclosed apparatus employs a carrier moving at uniform rate whereon first and second quantities per unit time of loose fibrous material are conveyed by air and deposited on first and second different portions of the carrier. The uneven distribution of material on the foraminous carrier is achieved by providing the air stream with a velocity profile in which certain portions have a higher velocity than the adjoining portions and convey a greater amount of material to associated portions of the carrier, by creating a greater vacuum or suction behind the associated portions of the foraminous carrier than behind adjacent portions so as to draw the air through the screen at the same rate as it arrives at the screen. This in turn is achieved by shielding a portion of the carrier from the air stream while deflecting the air stream toward the unshielded portion.

As shown in FIG. 5 of the '813 Lee et al. patent, baffles 46 are provided to constrict the conduit through which air is delivered to the carrier, with valves 48 being provided to permit the establishment of a lower pressure behind certain portions of the carrier than behind adjacent portions. The baffles and valves are both selectively operable to provide the web with a predetermined profile or cross-sectional configuration. The web produced by such apparatus, as disclosed in column 4, lines 1–3, has a raised or thick center portion flanked by substantially thinner edge portions. Thus, baffles are provided upstream of the forming surface and valves downstream from the forming surface, with respect to the path of the air flow therethrough. Each of the baffles is in the form of a flat plate beveled at its innermost end and positioned in a slot defined by flanges, which by virtue of the inclination of the flanges, cause the baffles to extend inwardly from opposite sides of the central conduit and be inclined in the direction of flow of the air stream. Accordingly, the baffles constrict the conduit within the delivery duct to narrow the air stream to a centrally disposed vertically oriented flow and thereby increase velocity of the air stream in the central area of the conduit.

The foraminous carrier is supported by a vacuum box which also serves to control the passage of air through the carrier. The vacuum box includes a grid plate provided with a plurality of openings which affords communication between the vacuum chamber and the surface of the grid plate, thereby creating a section which removes air arriving at the surface of the plate. Each opening in the grid plate has associated therewith a valve which permits selective control of air pressure at each opening and, consequently, permits variations in the degree of suction across the grid. The web formed on the carrier screen is removed therefrom by a take-off roll associated with nozzles proximate thereto which direct jets of air outwardly through the carrier screen thereby assisting in the separation of the web from the screen, and cleaning the screen of adhering fibrous particles.

U.S. Pat. No. 3,598,680 to C. A. Lee discloses a tandem air former for forming a fibrous web of non-uniform cross-sectional thickness, by air-laying fibrous material at a first station and then air-laying additional fibrous material at a second station downstream from the first to overlap at least partially the fibrous material deposited at the first station. A pressure differential is maintained across the web during formation, to cause air to flow through the thicker portion of the web as well as the thinner portions at substantially the same rate as it approaches the web. The air flow passageway to the foraminous carrier is defined in part by deckle plates which are adjustable transversely of the web being formed, i.e., the respective opposed deckle plates may be shifted toward or away from one another to vary the width of the air stream passing between them and, in consequence, the width of the pad being deposited on the web.

U.S. Pat. No. 3,975,222 to F. K. Mesek discloses a disposable diaper assembly comprising an absorbent fibrous panel which is double contoured, being centrally contoured in the transverse and longitudinal directions to produce a smooth peak on one major surface. Two rolls of compacted wood are provided to feed a source of short cellulosic fibers to a grinding mill from which a stream of fibers is blown downwardly through a duct onto a belt as a layer. The patent discloses that the duct may be baffled to allow more fibers to be concentrated at the central portion of the web. Another method comprises grinding fibers at one station and depositing them to produce a continuous web at the maximum width desired and grinding fibers at another station and depositing them downstream along a band of lesser width on top of and along the median of the first continuous web. A longitudinal contour of the fibrous web is achieved by varying the speed at which fibers are deposited on the belt, so that by decreasing the deposition rate the marginal areas of reduced thickness are produced and correspondingly, by increasing the deposition rate, the thickened central contour portion is produced. The contour thickness is preferably formed to provide a ratio of apex thickness to corner thickness in the range of 1.5:4.

U.S. Pat. No. 3,994,047 to C. A. Lee et al. discloses apparatus for making two-layer composite pads formed simultaneously on a twin wire arrangement, with the units of one layer being of hourglass and the other, ovate in shape. The layers are formed on respective foraminous carriers in a forming chamber. In the disclosed system, it is necessary to keep the respective forming screens in register with one another inasmuch as the webs formed thereon are subsequently joined to form the aforementioned composite. For such purpose, the respective forming screens have registration indicia which may be sensed as, for example, by an electric eye, to indicate any misregistration whereby the appropriate tension roll for the respective forming screen is adjusted to maintain registration. In order to drive air through the laydown fibrous web layers at the same rate at different portions of the forming path, the pressure differential and the respective forming layers increase in the direction of travel of the carrier screens by separately controlled air flow through suction boxes associated therewith. Each of the suction boxes includes a damper for controlling the rate of flow of air through each of the boxes. The forming chamber also has a perforated wall opening through which additional air may be admitted to the forming chamber.

A removal means is provided at the exit end of the forming chamber to remove any excess fibers as deposited on the respective carriers. This removal means includes a snout 110 which in turn includes a septum and walls defining openings through which air is sucked by a blower at relatively high velocity. The walls of the snout are disposed relatively close to the tops of formed layers of fibers to provide a rush of air over the exposed surfaces thereof. This shears fibers from the surfaces of the layers and entrains the fibers in the air stream removed therefrom. The foraminous carrier screens in this system include open areas on which the respective fibrous web components are formed, the areas outside of such patterned open areas being impervious (impermeable) to air flow.

U.S. Pat. No. 4,016,628 to C. G. Kolbach discloses an apparatus for forming a fibrous web which includes a medial portion integrally joined through the randomly arranged fibers thereof to flanking side portions and flanking end portions, the medial portion having a greater basis weight and thickness than the respective flanking side and end portions. The patent discloses at column 3, lines 29–40 that the higher basis weight medial portion of the fibrous web can be substantially uniform in basis weight or can be profiled, e.g., with the center section of the medial portion being provided with a greater basis weight of fibers than the flanking end sections (for use as disposable diapers for girls and, alternatively, a forward section of the medial portion being provided with a greater basis weight of fibers therein than a rearward section thereof, as when the fibrous web is used as a disposable diaper for boys). In addition, it is disclosed at column 3, lines 41–47 that the specific shape of the medial portion can be varied within wide limits, such as being substantially rectangular or contoured to include a reduced width crotch region which provides a more conformable structure in the perineal region of a wearer.

Embodiments of the product fiber web are shown in FIGS. 11–16 of the Kolbach patent, wherein the medial portion of the web is profiled to itself to have different basis weights in different predetermined sections thereof, such as the medial portion having a center section of greater basis weight than the adjoining end sections of the medial portion (FIGS. 11, 13 and 15) and a configuration wherein a greater basis weight section of the medial portion is provided on the forward half thereof (FIGS. 12 and 16).

The disclosed apparatus employs a foraminous forming surface and at least one vacuum box under a discrete section of the forming surface. The foraminous forming surface and the vacuum box are moved in registration with each other through a web forming area so that the same region of the foraminous forming surface is always in overlying relationship to the vacuum box. In operation, an air suspension of fibers is directed onto the surface of a condenser roll assembly, having a foraminous forming surface disposed thereon with circumferentially spaced, three-dimensional compartments therein. Downstream therefrom may be disposed embossing rolls having corresponding surface recesses therein for embossing the fibrous web, to provide surface contours thereon which channel liquids so that the full absorbent capability of the fibrous web is utilized.

The condenser roll assembly includes an air-pervious condenser roll including a perforated cylindrical metal shell and a porous screen secured about the periphery of the shell. The three-dimensional compartments are established by providing discrete cutout regions in the porous screen and cylindrical metal shell and securing a foraminous member to the lower surface of the shell to bridge each cutout region and thereby form the bottom wall of the three-dimensional compartment. In this manner, the porous screen outside the three-dimensional compartments and the foraminous member constituting the lower surface thereof together provide a forming surface for the condenser roll. A vacuum box assembly is mounted within the condenser roll secured to a driving axle so as to be concurrently rotated with the cylindrical shell. The vacuum box assembly includes a plurality of circumferentially spaced vacuum boxes attached to a cylindrical hub, with the outer edges of the sidewalls of the vacuum boxes defining an opening into the vacuum box of the same shape as the three-dimensional compartments, when aligned therewith. Since the cylindrical shell and the vacuum box assembly are concurrently rotated at the same angular velocity, each vacuum box will underlie its respective compartment throughout the entire path of rotation. Removal of the formed web from the condenser roll is effected by terminating the partial vacuum through the forming surface. This is achieved by a masking member circumferentially extending in coaxial manner with the condensing roll and the vacuum box assembly, and interposed therebetween. The masking member is perforated over a portion of its length and is imperforate on the lower section.

Accordingly, the condenser roll and vacuum box assembly during its travel will encounter the imperforate portion of the masking member, thereby blocking the vacuum imparted to the formed web, so that the web may be removed by a take-off conveyor to which vacuum is applied. The masking member is not rotated, so that the condenser roll and vacuum box assembly pass circumferentially adjacent to the masking member over its full circumferential extent. Vacuum is provided to the forming surface by suction through an annular passage in flow communication with the vacuum boxes. The portions of the interior of the condenser roll are in flow communication with a second annular passage with a reduced vacuum level being imposed thereon. The patent states at column 12, lines 56–62 that since the entire forming surface of the condenser roll is exposed to vacuum for the same period of time, a greater effective or total volumetric air flow will be established through the bottom walls of the three-dimensional compartments, which are subject to a greater partial vacuum than the surfaces flanking the three-dimensional compartments. This greater effective volumetric air flow results in the deposition of a greater weight of fibers in each of the three-dimensional compartments than on the foraminous surface regions surrounding the three-dimensional compartments. The drawings of this apparatus, such as FIG. 3, indicate the three-dimensional compartment to be relatively shallow and to be bounded by radially extending wall surfaces which appear to be perpendicular to the forming surface.

In a modified embodiment of the invention, as shown in FIGS. 17–19 of the patent, a masking member is employed in which the imperforate circumferential portion has at one end thereof "finger portions" which underlie the three-dimensional compartments at their extremities. These finger portions are followed circumferentially by a central blocking portion of the mask member which in turn underlies the central portion of the three-dimensional compartment when same is passed over the masking member. The circumferential extent of the finger portions is greater than the circumferential extent of the central blocking portion of the masking member, whereby the central region of the three-dimensional compartment will be exposed for a greater period of time to the vacuum, to achieve formation of thickened central portions of the three-dimensional compartments.

Finally, the patent states at column 15, lines 2–7 that "it is within the scope of this invention to provide a fluid impervious coating directly on the forming surface of the condenser roll in the form of a transverse stripe disposed intermediate adjacent three-dimensional compartments to achieve direct formation of discrete fibrous webs on the forming surface." It is apparent that this coating serves as a fiber deposition blocking means to segment the web during laydown, in discrete segments.

U.S. Pat. No. 3,518,726 to C. T. Banks discloses an apparatus for making sanitary napkins from fluff derived from wood pulp which has been disintegrated. A forming drum is employed which has on its cylindrical surface a series of planar chord-like plate members which are perforated, each plate having perforations more closely spaced relative to one another in the central portion of the plate as compared to the end segments of the chord-like plates, wherein the perforations are more distantly spaced relative to one another. The forming drum is in gas flow communication with vacuum suction means, whereby areas of fluff deposited on the drum compartments are of greater thickness at their centers relative to their ends, due to the arcuate shape of the side plates defining each compartments on the drum periphery. In addition, more fluff collects in the central regions of the cavities than in the end regions due to the fact that the spacing between holes is less in the central regions than in the end regions, so that the resulting pad is thicker in its central region.

This patent also discloses an embodiment wherein a compressed, high-density segment is provided for embedment in one of the flat faces of the pad. In this embodiment, a second assembly takes disintegrated pulp fibers and collects some on a forming drum which is composed of a cylinder of perforated sheet material, with a vacuum box in communication with a central opening through the rotatable drum for maintaining vacuum therein. An end closure plate portion extends across and within the forming drum, being sealed with respect to the inner surface thereof. In this fashion, only about one-half of the forming drum has suction applied to it. This forming drum is in close-spaced relationship to a similar forming drum, whereby each collects fluff on its exterior surfaces for discharge therefrom between the drums in the form of a continuous batt. The batt then is debulked between compression rolls and indented at spaced intervals, following which the batt passes through an embossing assembly which provides a pattern of pyramidal-shaped depressions therein. The batt then is cut into segments and transmitted by conveyor means to the first-mentioned forming drum, on which the high-density segment is centrally disposed on the forming cavity and overlaid with fluff. The resulting pads, containing the high-density segments on their lower faces, are cut in a cutter assembly and passed to a wrapping means whereon a gauze web is folded around the individual pads, pleated and severed to form the individual sanitary napkin.

U.S. Pat. No. 5,983,457, to Toney et al., discloses an inlet plenum apparatus for delivering a uniform mass of airborne cellulose for other natural and synthetic fibers—including all forms of super absorbent, used for absorbent applications such as disposable diapers—to an apparatus employing a rotating drum containing a foraminous pad forming system and depositing it on the pad forming system in a uniform layer. The apparatus employs an inlet plenum having a specific shape to slow the air flow from the conveying line into the forming area by specified amounts to result in improved uniformity of the pad.

As is apparent from the foregoing, prior references have presented a variety of systems for producing variant basis weight articles by air-laying of fibers, as well as numerous means of removing the laid fibrous article from the forming surface. Yet, all of these proposed techniques are characterizable to some degree by deficiencies in terms of the mechanical complexity involved as well as in deficiencies of the absorbent material which is produced resulting in corresponding cost inefficiencies and/or low product quality.

Insofar as the latter point, i.e., the character of the absorbing material produced by laying of the fibrous material, is concerned, it is highly desirable in applications such as the production of absorbent pads for disposable diapers to provide a gradation of basis weight, with a higher basis weight being provided forward of the lateral center line (crotch fold line) of the article, as compared to the rear portion thereof and wherein the basis weight is proportionately distributed in a predetermined ratio to yield an optimal absorbency profile. Further, it is highly desirable to provide a process which produces absorbent articles with optimal absorbency profiles, without the corresponding mechanical complexity and/or cost inefficiencies described in prior references.

SUMMARY OF THE INVENTION

It is an object of the invention to provide an apparatus which provides, in a cost-effective manner, an absorbent article having an optimal absorbency or optimal absorbency profile.

It is a further object of the invention to provide a method which provides, in a cost-effective manner, an absorbent article having optimal absorbency or an optimal absorbency profile.

It is an even further object of the invention to provide an article which has multiple zones, each having a different absorbent capacity corresponding to a designated area on the article so that the article has an optimal absorbency or an optimal absorbent profile.

One embodiment of the invention is an apparatus for preparing an absorbent article, which comprises: a forming surface having a first predetermined zone with a first air permeability and a second predetermined zone with a second air permeability, said first air permeability being different from said second air permeability; means for placing particles into an airflow; and means for guiding the airflow containing said particles through the forming surface to deposit the particles on said forming surface.

A further embodiment of the invention is an apparatus for preparing an absorbent article, which comprises: a forming surface having a first predetermined zone and a second predetermined zone, said first predetermined zone having a first plurality of openings defining an area of about 30% to about 85% of the total area of the first predetermined zone, said second predetermined zone having a second plurality of openings defining an area of about 5% to about 25% of the total area of the second predetermined zone; a rotating drum on which the forming surface is mounted; means for placing particles into an airflow; and means for guiding the airflow through a forming chamber and the forming surface to deposit the particles on said forming surface.

An even further embodiment of the invention is a method for preparing an absorbent article, comprising the steps of: (a) placing particles into an airflow; (b) transporting the particles in the airflow through a forming chamber to a forming surface; (c) depositing the particles on said forming surface, said forming surface having a first predetermined zone with a first air permeability and a second predetermined zone with a second air permeability, and said first air permeability being different from said second air permeability.

A still further embodiment of the present invention is a method for preparing an absorbent article, comprising the steps of: (a) placing particles into an airflow; (b) transporting the particles in the airflow through a forming chamber and to a forming surface mounted on a section of a rotating drum; and (c) depositing the particles on the forming surface, said forming surface having a first predetermined zone and a second predetermined zone, said first predetermined zone having a first plurality of openings defining an area of about 30% to about 85% of the total area of the first predetermined zone, and said second predetermined zone having a second plurality of openings defining an area of about 5% to about 25% of the total area of the second predetermined zone.

Another embodiment of the present invention is an absorbent article, which comprises: a first predetermined area having a first AUL; a second predetermined area having a second AUL; and wherein the ratio of the first AUL to the second AUL is about 1.25:1 to about 5:1.

Still another embodiment of the present invention is an absorbent article, which comprises: a first predetermined area having a first FVAUL; a second predetermined area having a second FVAUL; and wherein the ratio of the first FVAUL to the second FVAUL is about 1.25:1 to about 5:1.

Yet another embodiment of the present invention is a formed fibrous article prepared by a process comprising the steps of: (a) placing particles into an airflow; (b) transporting the particles in the airflow through a forming chamber and to a forming surface mounted on a section of a rotating drum; and (c) depositing the particles on the forming surface, said forming surface having a first predetermined zone and a second predetermined zone, said first predetermined zone having a first plurality of openings defining an area of about 30% to about 85% of the total area of the first predetermined zone, and said second predetermined zone having a second plurality of openings defining an area of about 5% to about 25% of the total area of the second predetermined zone.

DETAILED DESCRIPTION OF THE PREFERRED EMBODIMENTS

As used herein, "absorbency" refers to the functional capacity and the rate at which absorption occurs as measured by absorption under load (AUL) or finite volume absorption under load (FVAUL). "Air permeability", as used herein, refers to the amount of air which the surface permits to pass through during a specified amount of time relative to another surface having the same total area as the first surface.

As used herein, the term "absorbent article" refers to articles that absorb and contain exudates, and more specifically refers to articles which are placed against or in proximity to the body of the wearer to absorb and contain various exudates discharged from the body. A non-exhaustive list of examples of absorbent articles includes diapers, diaper cores, diaper covers, disposable diapers, training pants, feminine hygiene products and adult incontinence products. The term "disposable article" refers to absorbent articles that are intended to be discarded or partially discarded after a single use, i.e., they are not intended to be laundered or otherwise restored or reused. The term "unitary disposable absorbent article" refers to a disposable absorbent article that is essentially a single structure (i.e., it does not require separate manipulative parts such as a diaper cover and insert). As used herein, the term "diaper" refers to an absorbent article generally worn by infants and incontinent persons about the lower torso.

The claims are intended to cover all of the forgoing classes of absorbent articles, without limitation, whether disposable, unitary or otherwise. These classifications are used interchangeably throughout the specification, but are not intended to limit the claimed invention. The invention will be understood to encompass, without limitation, all classes of absorbent articles, including those described above. Preferably, the absorbent core is thin in order to improve the comfort and appearance of a garment. The employance of thin, comfortable garments is disclosed, for example without limitation in U.S. Pat. No. 5,098,423 to Pineiak et al. which is herein incorporated by reference.

Figure 1:
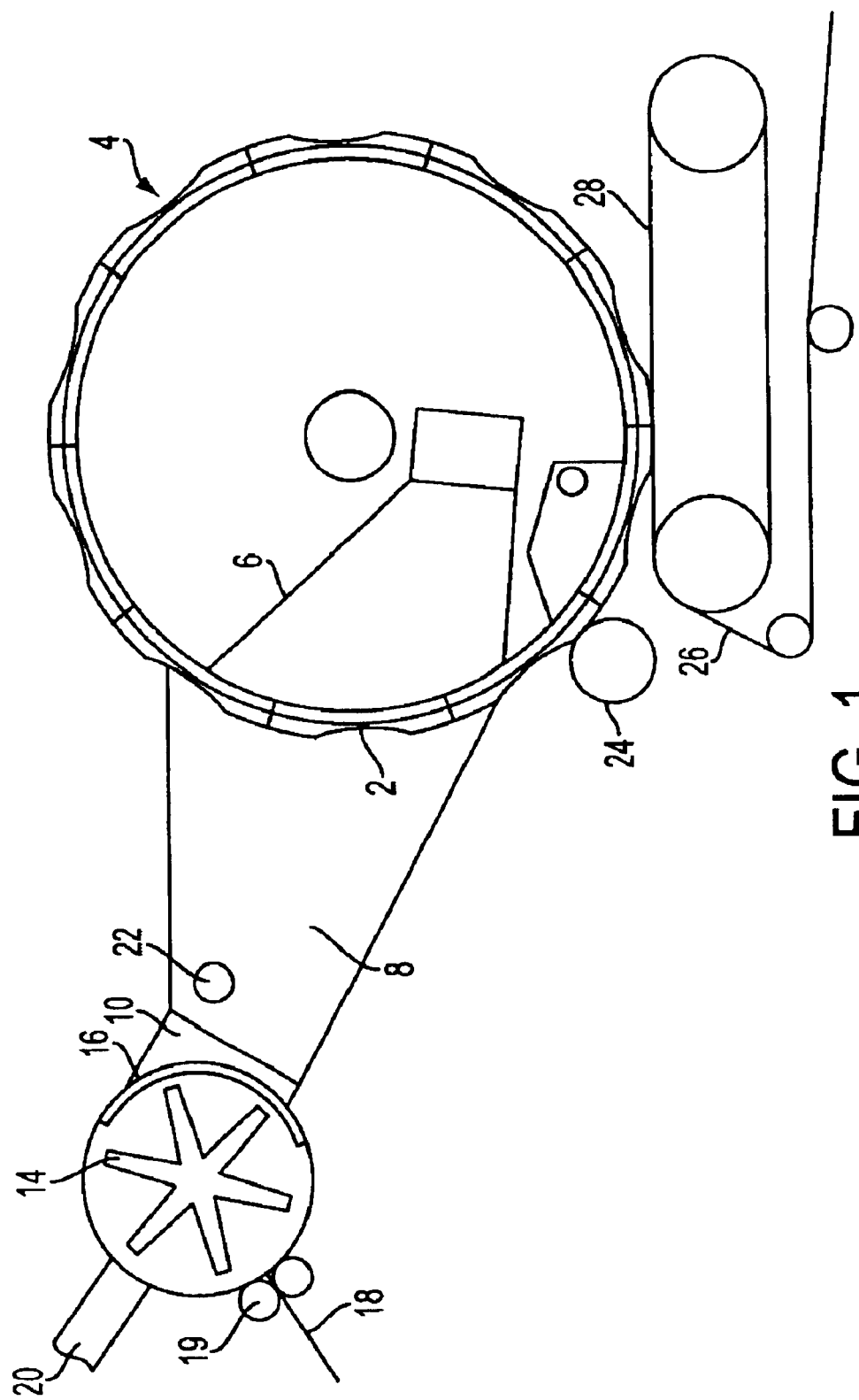
FIG. 1 is a side elevational view of apparatus employed in one method of manufacturing an absorbent article.

Referring to the drawings, FIG. 1 shows the forming surface 2 which is mounted on the drum assembly 4. A forming chamber 8 is attached to the outlet shroud 10 and feeds an air stream to the forming surface on the drum assembly 4.

A hammermill having a blade or a plurality of blades receives a fiber board 18 at a pair of feed roles 19. Any blade or plurality of blades capable of fiberizing the fiber board are contemplated by the invention. Non-limiting exemplary blades include steel, metal alloy and carbide tipped blades. Preferably, the blades are carbide tipped blades. The feed roles 19 feed the fiber board to the carbide tip blades 14 which disintegrate the board into particles which are carried into the outlet shroud 10 by an air stream originating from an air inlet scoop 20 which is connected to the hammermill 12 at a hammermill screen 16.

The forming chamber 8 contains a nozzle 22 having an outlet into the interior of the forming chamber 8 through which a substance such as a super absorbent polymer ("SAP"), for example without limitation, may be sprayed or injected into the air stream passing through the interior of forming chamber 8 where the substance will combine with the particles contained in the air stream.

The drum assembly 4 has an inner vacuum chamber 6 positioned in such a manner as to create a vacuum at the forming surface on certain portion or portions of the drum assembly 4. Mounted to the exterior of the drum assembly 4 is a scarfing roll 24 which is located in close proximity to the forming surface 2. A conveyor belt 28 is located adjacent to and beneath the drum assembly 4 and optionally contains tissue layers 26 for receiving the absorbent article formed on the forming surface when the article is released from the vacuum of the inner vacuum chamber 6 after passing through the scarfing role 24. Thus, once the drum assembly 4 rotates so that the absorbent article formed on the forming surface 2 is directly over the conveyor belt, the absorbent article is deposited onto the conveyor belt. For example, the absorbent article may be processed into a diaper, without limitation.

The conveyor belt 28 transports the absorbent article for further processing. For example, the absorbent article may be processed into a diaper, without limitation.

Figure 2A:
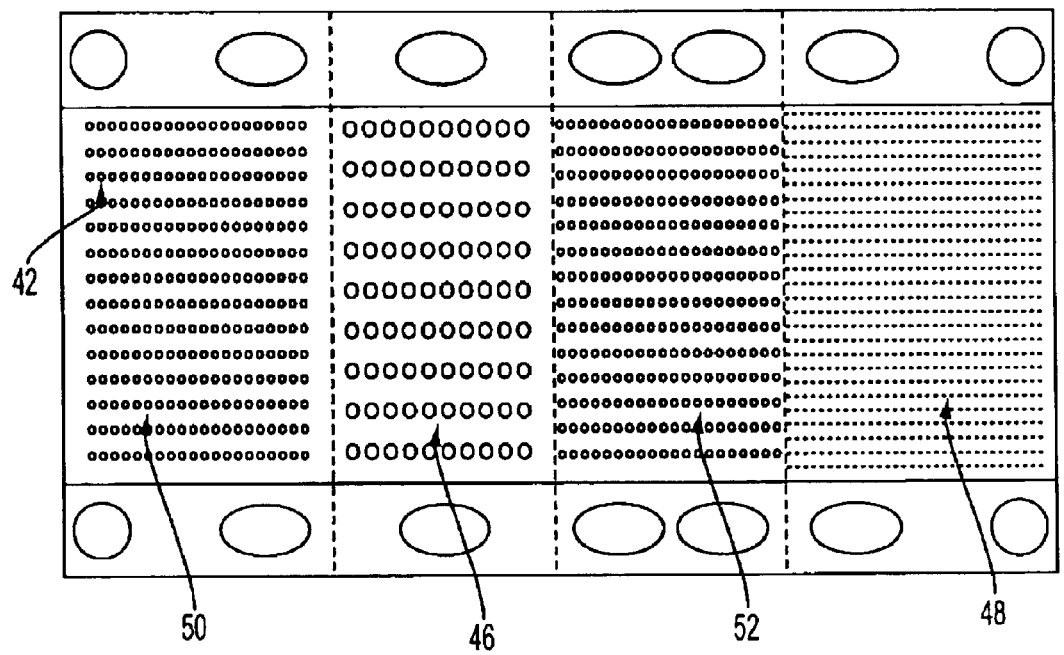
FIG. 2A is a plan view of a forming screen having four predetermined zones.
Figure 2B:
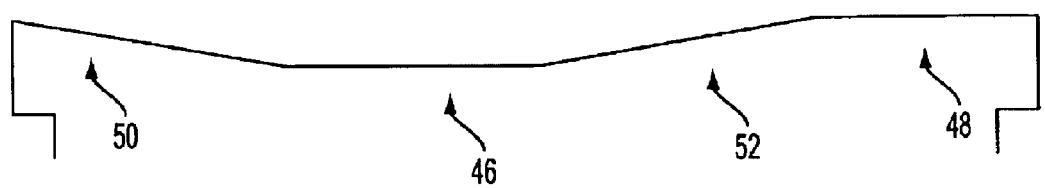
FIG. 2B is a side view of the forming screen of FIG. 2A.

Referring to FIG. 2A along with FIG. 1, a plurality of forming surfaces 2 (FIG. 1) are secured to a drum assembly 4. One of the plurality of forming surfaces is illustrated in FIGS. 2A and 2B. Forming surface 2 is divided into four separate zones, each containing perforations 42 defining an open area through which air passes giving a certain air permeability based upon the diameter and number of holes or perforations 42 within each zone and/or the thickness of the sheet metal. A first zone 46, which corresponds to the front of the absorbent article being prepared, has perforations 42 in a sufficient number and of a sufficient diameter to define an open area, through which air passes, of about 30% to about 85%, preferably about 40% to about 60%, more preferably about 45% to about 55%, and even more preferably about 49% of the total area of the first zone. A second zone 48 corresponds to the back of the absorbent article being prepared. The second zone 48 has perforations 42 in a sufficient number and of a sufficient diameter to define an open area, through which air passes, of about 5% to about 25%, preferably about 10% to about 22%, more preferably about 15% to about 20%, and even more preferably about 15%, of the total area of the second zone. A third zone 50, which defines a gradual transition from the first zone to the second zone, contains perforations 42 of varying diameter and/or number sufficient to provide a gradually decreasing open area from the first zone to the second zone. Likewise, a fourth zone 48, which defines a gradual transition from the second zone to the first zone, contains perforations 42 of varying diameter and/or number sufficient to provide a gradually decreasing open area from the second zone to the first zone.

The forming surface 2, while being permeable to air, is substantially impermeable to the solid materials carried in the airflow. By use of the term "air", it is contemplated that other vapors, gases or mixtures thereof may be used in place of air. The forming surface 2 may be in the form of a screen, a mesh, a grid, a matrix, or any selectively permeable form, and combinations thereof. The perforations 42 or openings in the forming surface 2 may be of any shape and combinations thereof. Preferably, the perforations 42 or openings are circular. The perforations 42 or openings may be of a wide variety of sizes provided the desired open area or air permeability is achieved. The forming surface 2 may be in any overall size or shape and may be bent or molded in various ways to achieve a wide variety of affects, as desired. Preferably the forming surface 2 is in a rectangular form, as shown in FIG. 2A and is bent as shown in the side view of FIG. 2B. It has been found that the varying air permeability of the forming surface unexpectedly results in an improved absorbent article having zones with differing absorbencies in a simple and cost effective manner while achieving a high level of precision.

The forming surface 2 may be composed of any material or combination of materials which can withstand the process conditions and produce the desired effect. Preferably, the forming surface is composed of sheet metal.

The perforations may be of any diameter. Preferably, the perforations in the sheet metal are a diameter ranging from about 0.020 to about 0.080 inches, more preferably the diameters of the holes range from about 0.030 to about 0.060 inches, even more preferably the diameters of the perforations range from about 0.036 to about 0.040 inches.

The perforations may be of uniform or non-uniform sizes. Preferably, the perforations are of uniform size.

Figure 3:
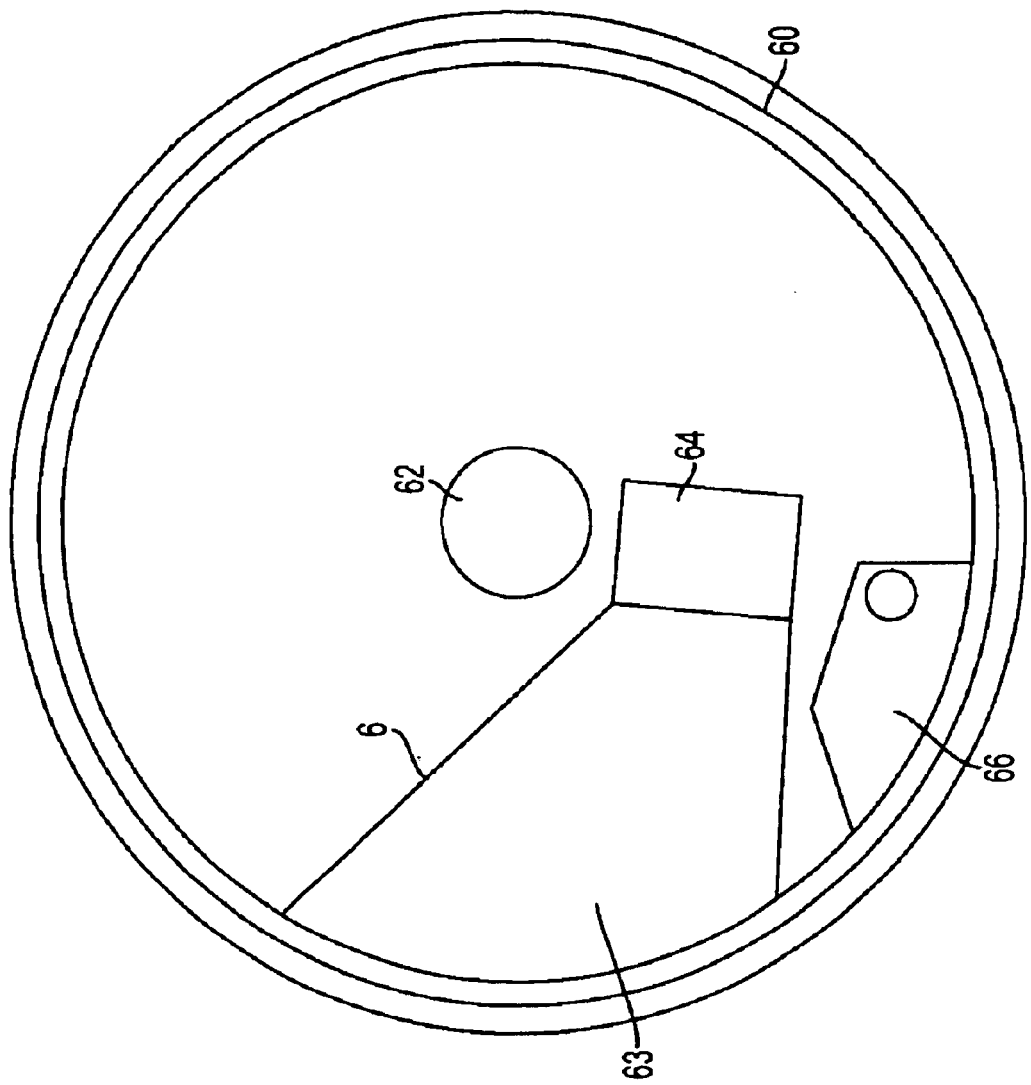
FIG. 3 is a cross-sectional view of the rotating drum assembly.

Referring to FIG. 3, the drum assembly 4 includes an outer cylinder upon which the forming surface 2 is mounted. The outer cylinder is supported and rotates around a central shaft 62. A vacuum or suction is drawn within the drum assembly 4 by means of an inner vacuum chamber 6. The vacuum created within the drum causes the airborne particles to adhere to the forming surface 2. As described above, the predetermined zones 46, 48, 50 and 52 on the forming surface 2 have different air permeability. Thus, the particles are deposited in varying amounts on the forming surface corresponding to the different zones. The basis weight of the fiber build up in each zone therefore is different from the other zones. This results in an absorbent article having a desired absorbent profile.

The inner vacuum chamber 6 includes a main chamber 63 and a main chamber outlet 64. The main chamber 63 receives the air flow from the forming chamber 8 (FIG. 1) after the air passes through the forming surface. The air then travels to the main chamber outlet 64. In this manner, a vacuum or suction is created on the forming surface 2 as described above. Outer cylinder 60 upon which the forming surface 2 is mounted rotates past the main chamber 63. After the forming surface passes the main chamber 63 it encounters the pad transfer chamber 66. The pad transfer chamber 66 does not receive the air flowing from the forming chamber 8. Therefore, there is no vacuum or suction beneath the forming surface 2 as the forming surface 2 rotates past the pad transfer chamber 66. Accordingly, the absorbent article formed on the forming surface is released from that surface and is able to be transferred to the conveyor belt, shown in FIG. 1, for subsequent processing.

Figure 4:
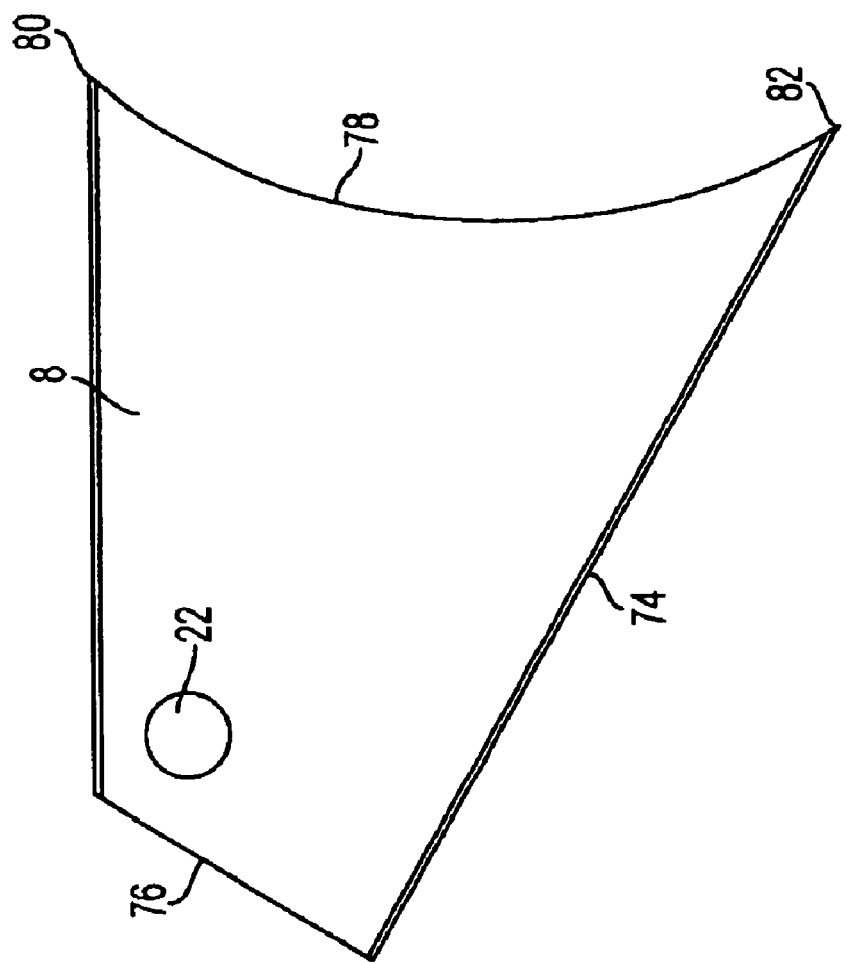
FIG. 4 is a side elevational view of the forming chamber.

Referring to FIG. 4, the forming chamber 8 is composed of a main air duct 74, an inlet opening 76 and an outlet opening 78. A nozzle 22 may be mounted on the main air duct 74 such that the nozzle penetrates into the interior of the main air duct 74 by means of an air tight seal. The nozzle 22 provides a means for injecting or spraying or providing in some other way a substance into the interior of the main air duct. The material may be a polymer such as a SAP, for example without limitation. The forming chamber 8 is mounted to the drum assembly at the outlet opening 78. The input opening 76 is attached to the outlet shroud 10 by means of an air tight connection.

Figure 5:
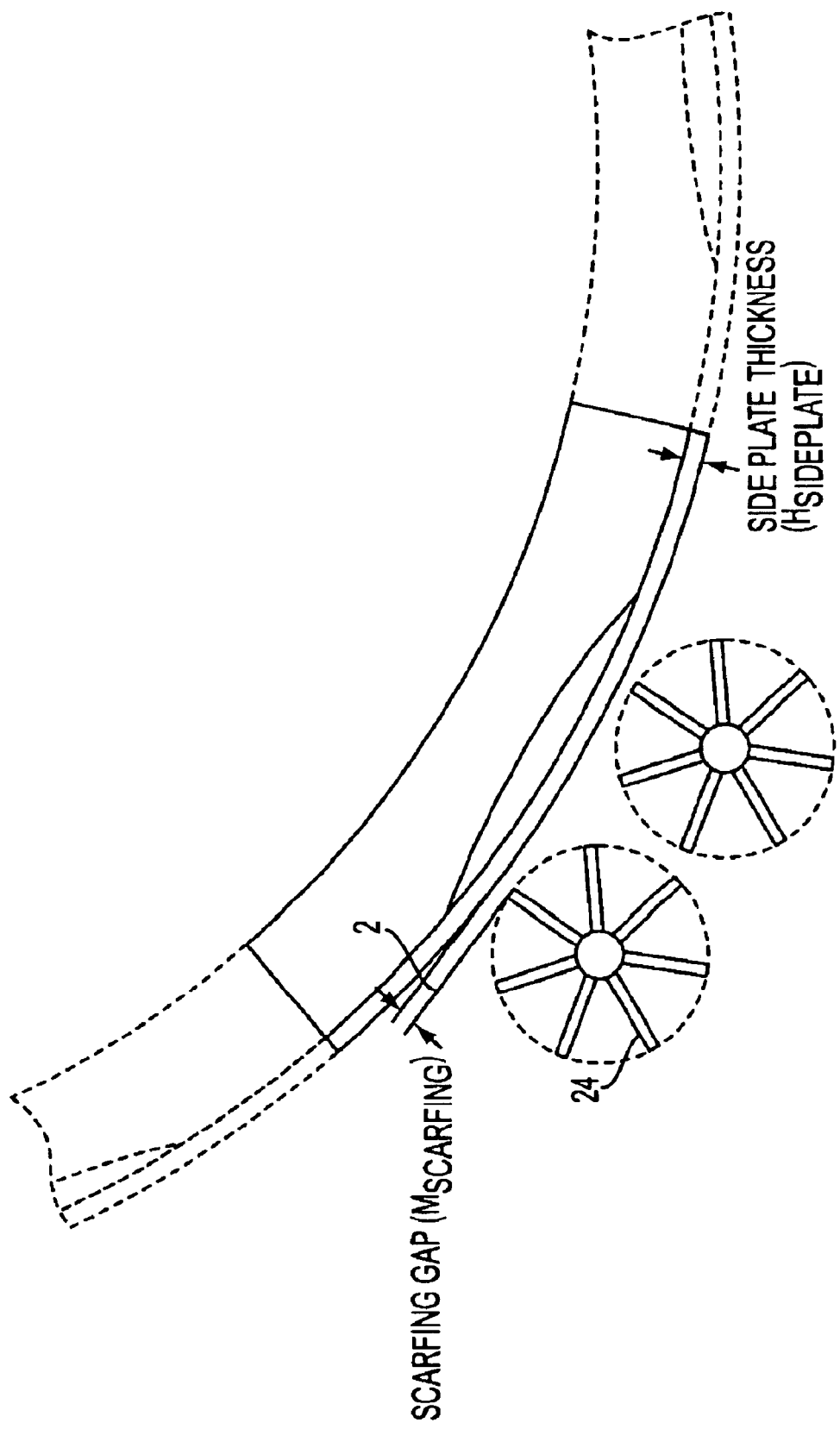
FIG. 5 is a side elevational view of the scarfing roll.

Referring to FIG. 5, optionally, a scarfing roll 24 is situated in close proximity to the drum assembly 4. The scarfing roll 24 is one or more rollers which comes into contact with the forming surface 2 and redistributes the material deposited on the forming surface 2 in a designated manner. Optionally, a return duct may recycle scarfed material by returning the material to the forming chamber 8. Use of any conventional scarfing roll or recycling means is contemplated by the invention. The use of scarfing rolls and recycling means in this manner is well within the skill of the art.

Figure 6:
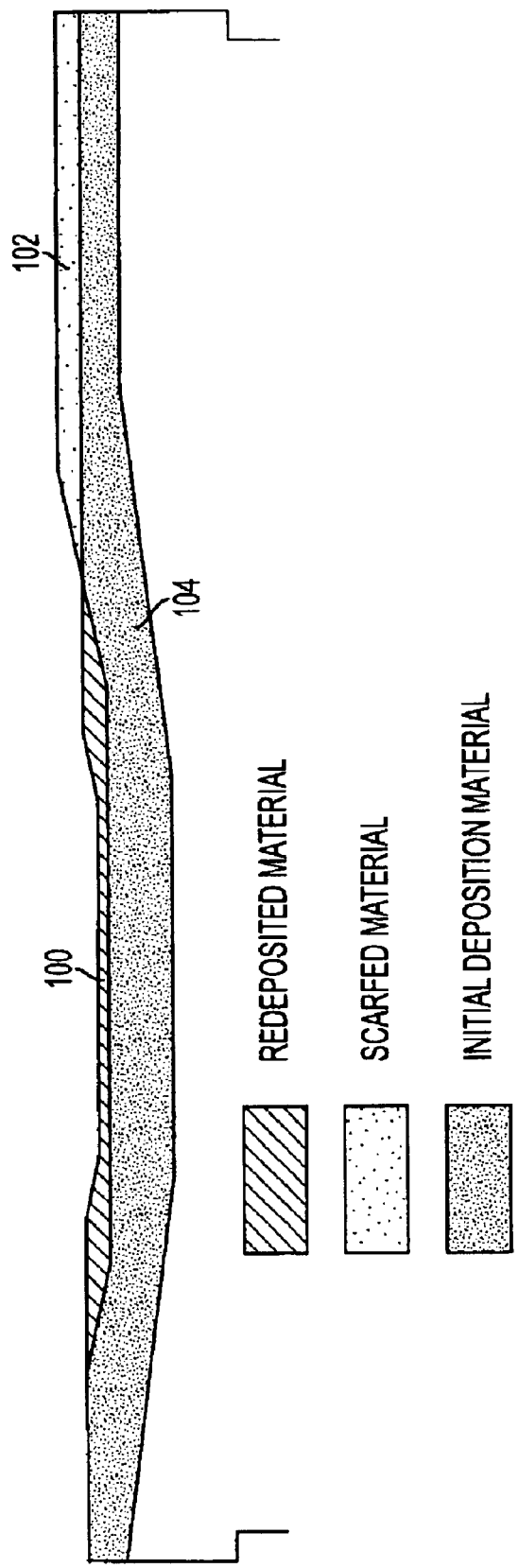
FIG. 6 is a cross-sectional view of the deposited particles after being scarfed by the scarfing roll.

FIG. 6 shows a cross-sectional view of the various components of the absorbent article on the forming surface 2 after the forming surface passes through the scarfing roll 24. As the figure shows, the scarfed particles 102 are redistributed by the scarfing roll 24 from the back to the front zone, thereby further reducing the basis weight (or absorbency) of the back section while increasing the basic weight (absorbency) of the front zone.

In this manner, the combination of the scarfing roll 24 with the forming surface 2 of the invention is a synergistic combination, as described below and illustrated in Graph 7.

Figure 7:
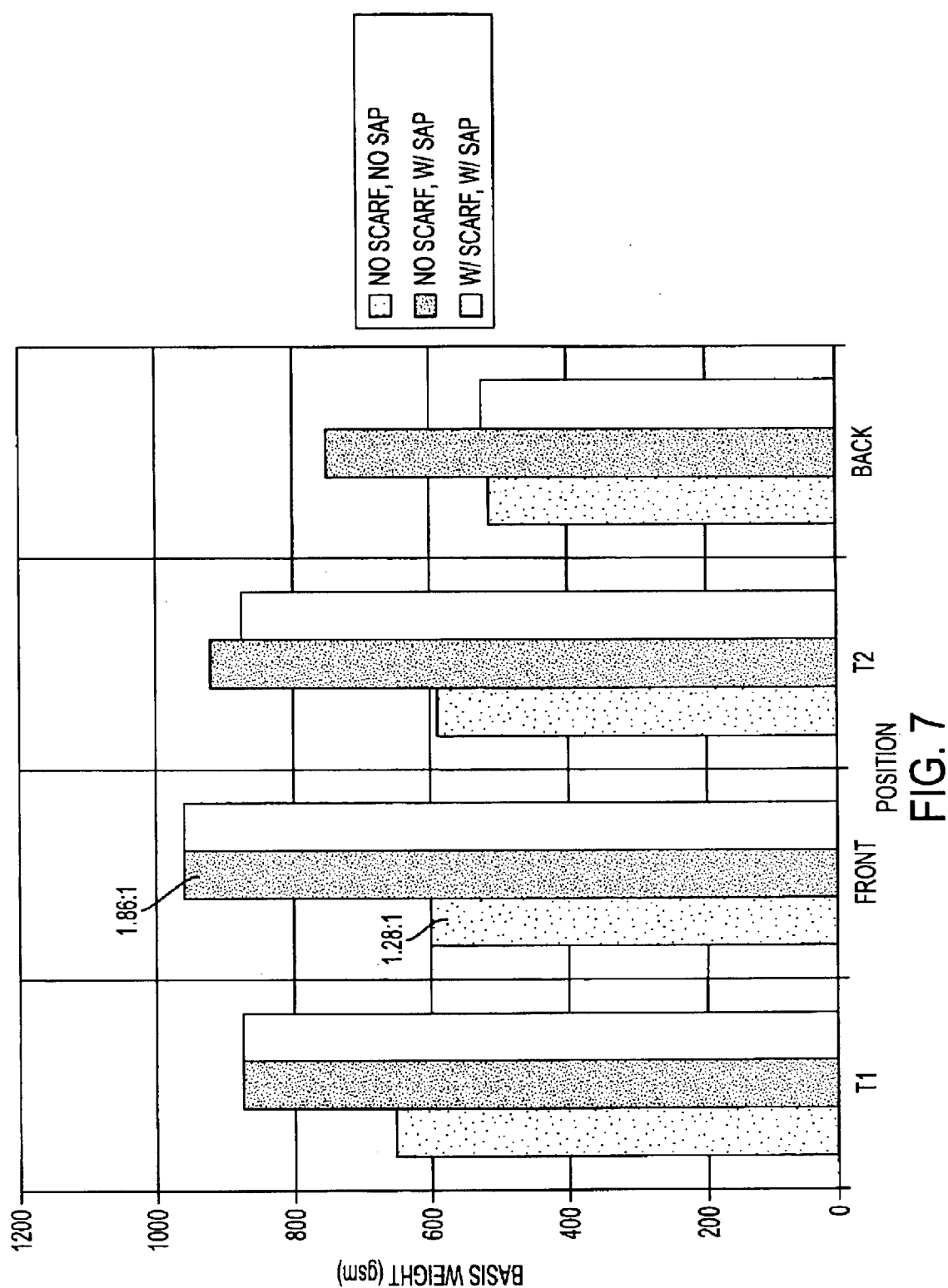
FIG. 7 is a graph which characterizes the article made in accordance with the method of the invention.

FIG. 7 is a graph, which corresponds to Table I below, illustrating the absorbency profile of the absorbent article when prepared in accordance with various preferred embodiments of the present invention. As shown in Table I and FIG. 7, when the process of the present invention is employed with no scarfing rolls and no SAP, an absorbent article is produced having a higher basis weight in the front than in the back through the use of the forming surface having different air permeability at corresponding predetermined zones. This demonstrates the effectiveness of the forming surface in selectively placing different amounts of the particles in different zones on the absorbent article. In particular, the basis weight in the front of the article was found to be 600 gsm while the basis weight in the back of the article was measured to be 500 gsm. When a SAP is applied during the process, again without use of the scarfing roll, an even greater difference between the front and back zones is achieved. In particular, the basis weight in the front zone was measured to be 950 gsm, whereas the basis weight in the back zone was found to be 750 gsm, or a 1.28:1 ratio between the front and back zones. When scarfing is used in the process along with a SAP, an even more dramatic result can be seen. As shown in the Figure and the Table, the front zone has a basis weight of 950 gsm, whereas the back zone has a basis weight of 500 gsm. This difference in basis weights represents a 1.86:1 ratio of the front basis weight to the back basis weight. Accordingly, the combination of the scarfing process with the use of the zoned forming surface of the invention represents a synergistic combination.

TABLE I

| | Transition Zone 1 (gsm) | Front Zone (gsm) | Transition Zone 2 (gsm) | Back Zone (gsm) | Weight Ratio of Front Zone to Back Zone |
|---|---|---|---|---|---|
| 1) No Scarf No SAP | 625 | 600 | 480 | 500 | 1.20:1 |
| 2) No Scarf With SAP | 840 | 950 | 910 | 750 | 1.28:1 |
| 3) With Scarf With SAP | 860 | 950 | 880 | 500 | 1.86:1 |

Figure 8:
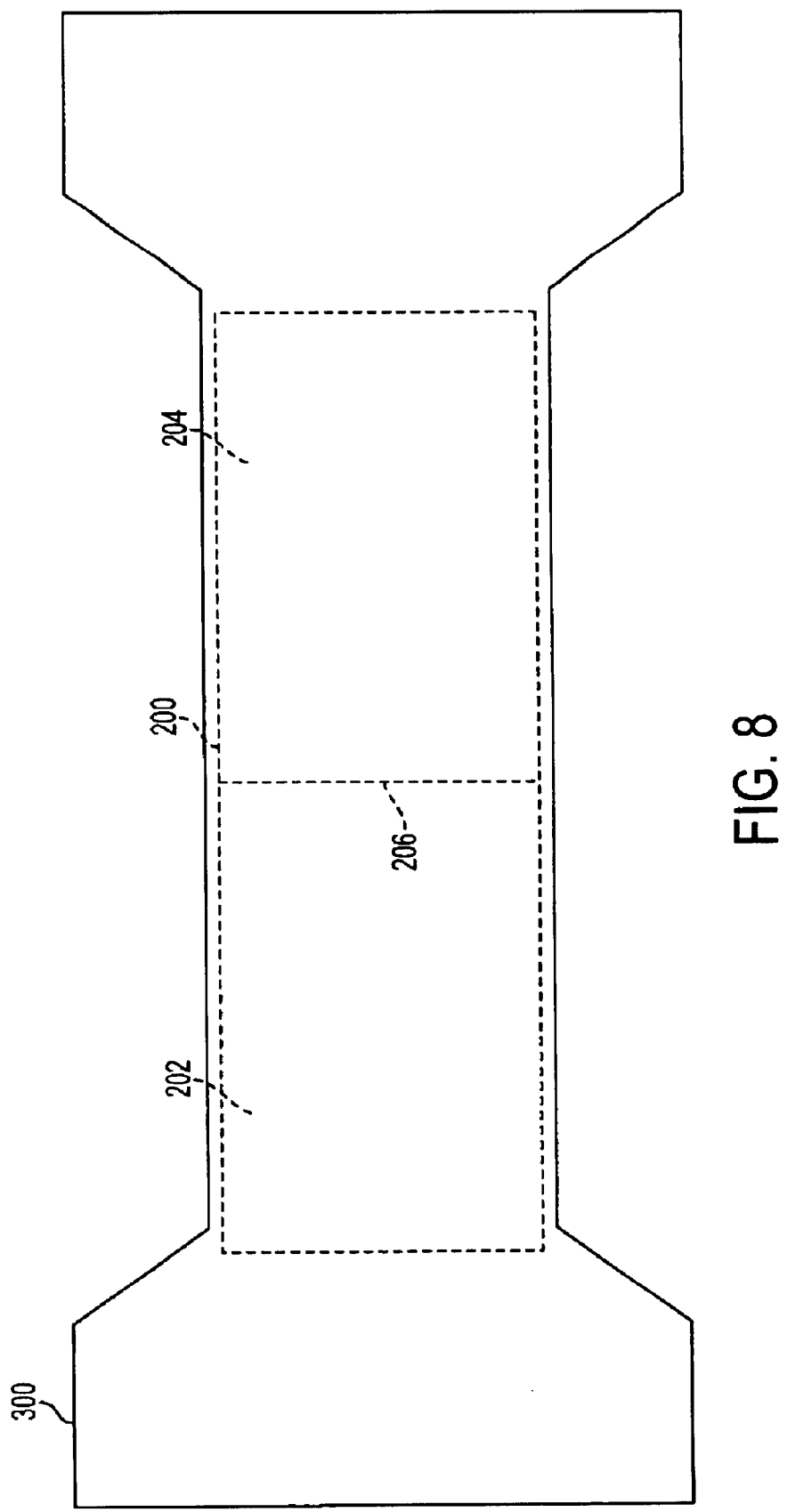
FIG. 8 is a plan view of the absorbent article of the preferred embodiments of the invention.
Figure 9A:
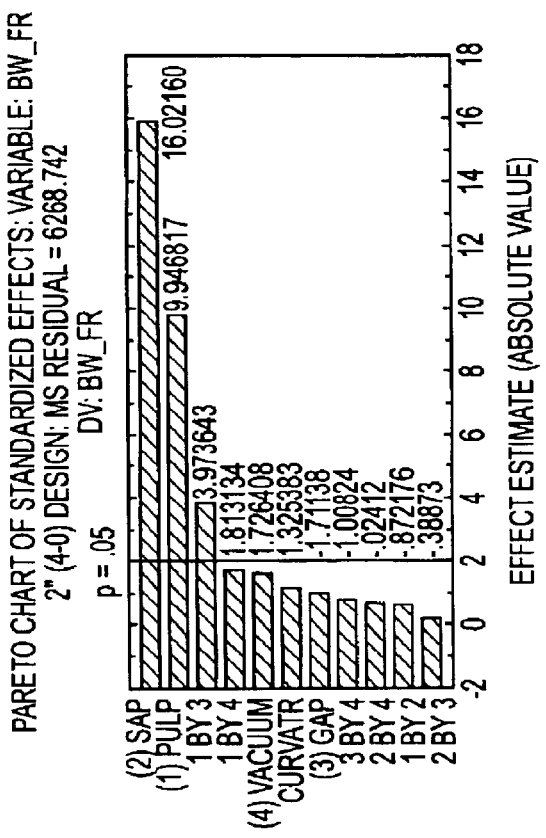
FIG. 9A is a pareto chart illustrating standardized effects for a transition zone on a forming surface in accordance with an implementation of the present invention.
Figure 9B:
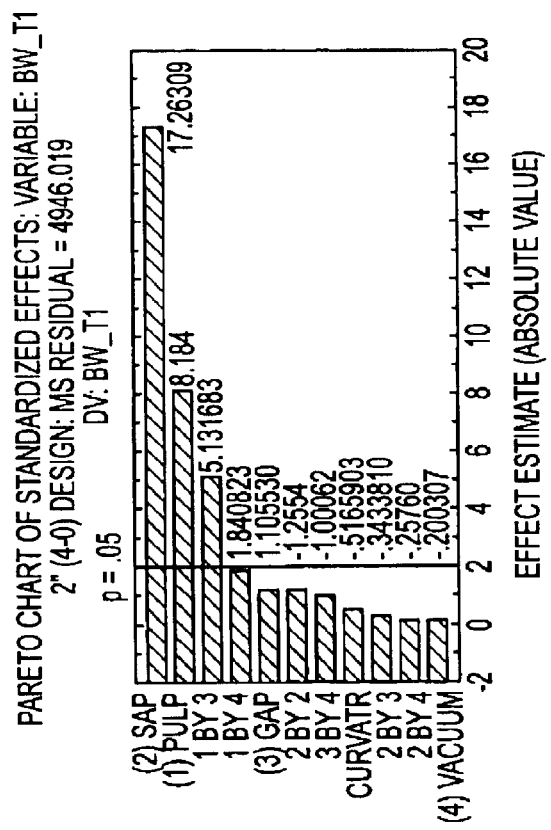
FIG. 9B is a pareto chart illustrating standardized effects for a front zone on a forming surface in accordance with an implementation of the present invention.
Figure 9D:
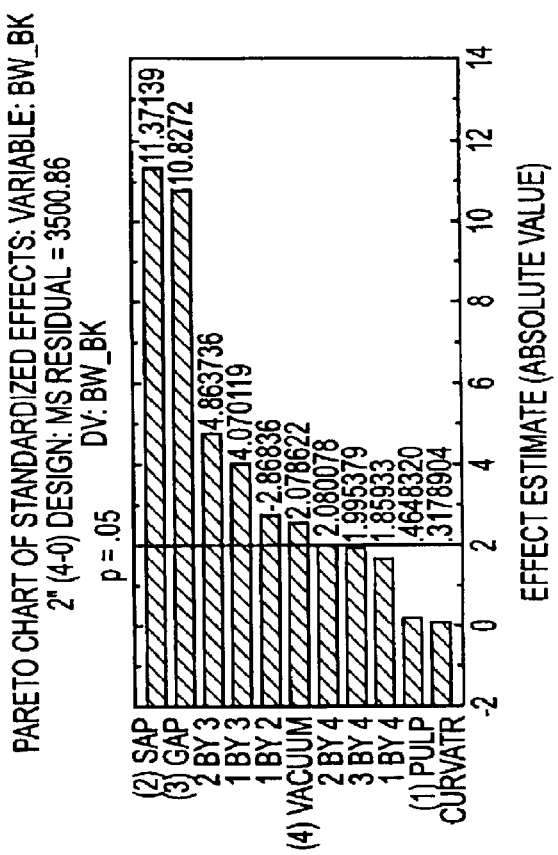
FIG. 9D is a pareto chart illustrating standardized effects for a back zone on a forming surface in accordance with an implementation of the present invention.
Figure 9C:
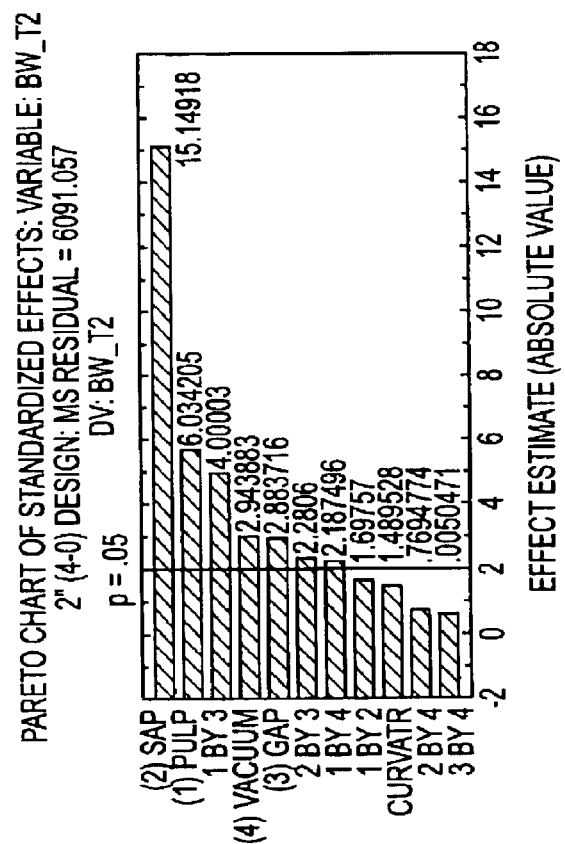
FIG. 9C is a pareto chart illustrating standardized effects for a second transition zone of a forming surface in accordance with an implementation of the present invention.
Figure 10:
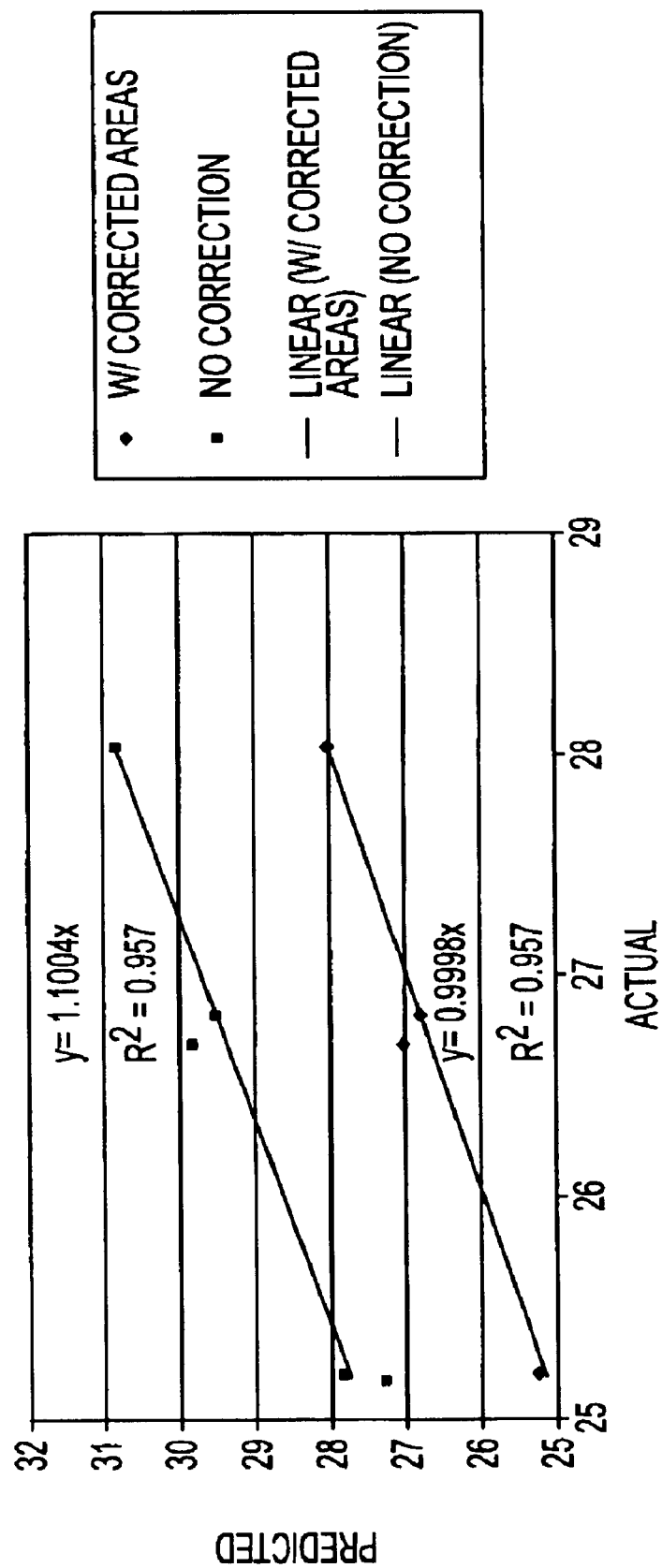
FIG. 10 is a graph illustrating the relationship between predicted and actual core weights in cores prepared in accordance with an implementation of the present invention.
Figure 11:
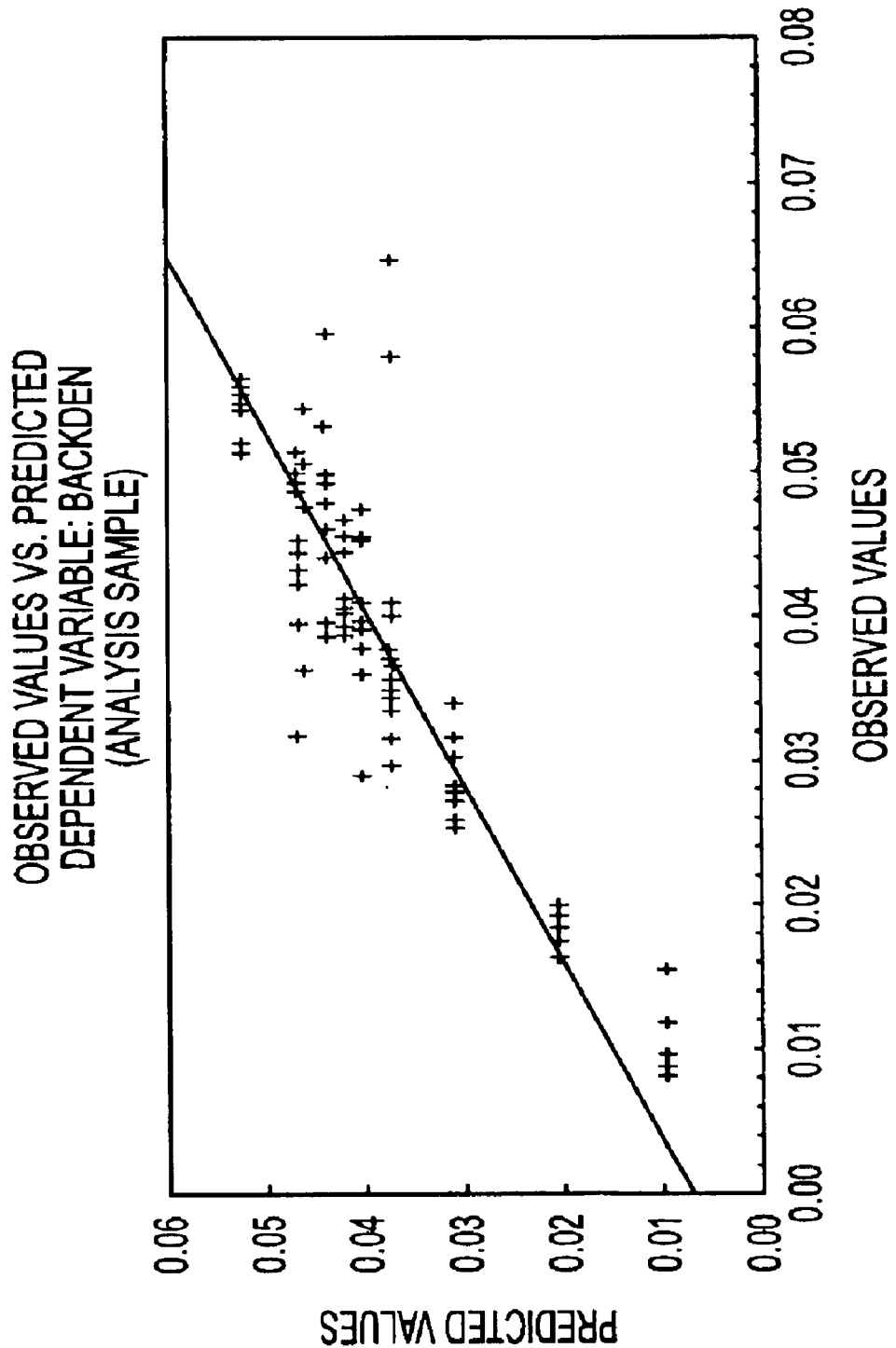
FIG. 11 is a graph illustrating the relationship between predicted values and observed values of pad density for a core formed on a forming screen having 0.036 inch opening, a front zone having 49% open area and a back zone having 15% open area, in accordance with an implementation of the present invention.
Figure 12:
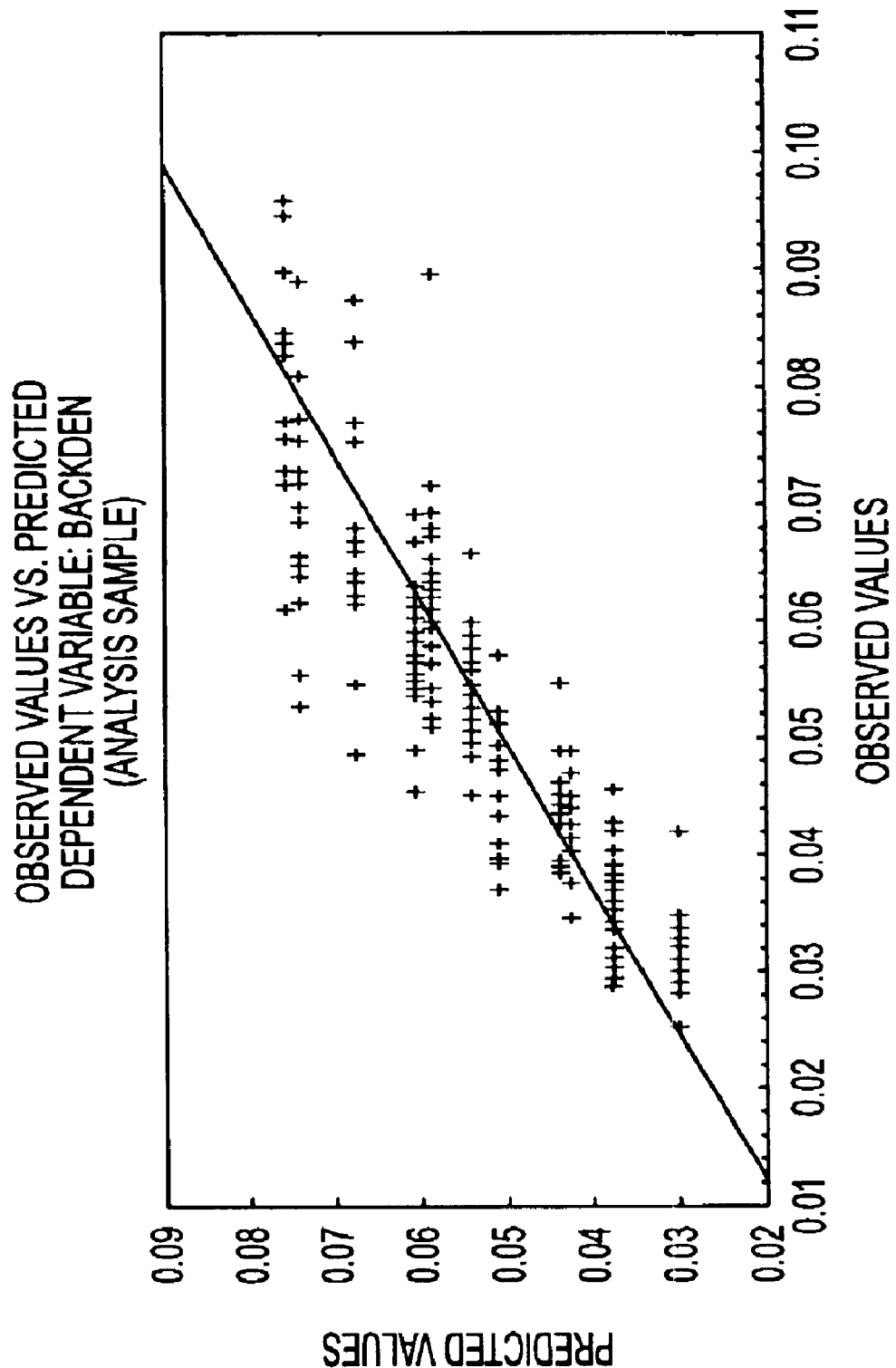
FIG. 12 is a graph illustrating the relationship between predicted values and observed values of pad density for a core formed on a forming screen having 0.040 inch openings, a front zone having 49% open area and a back zone having 20% open area, in accordance with an implementation of the present invention.
Figure 13:
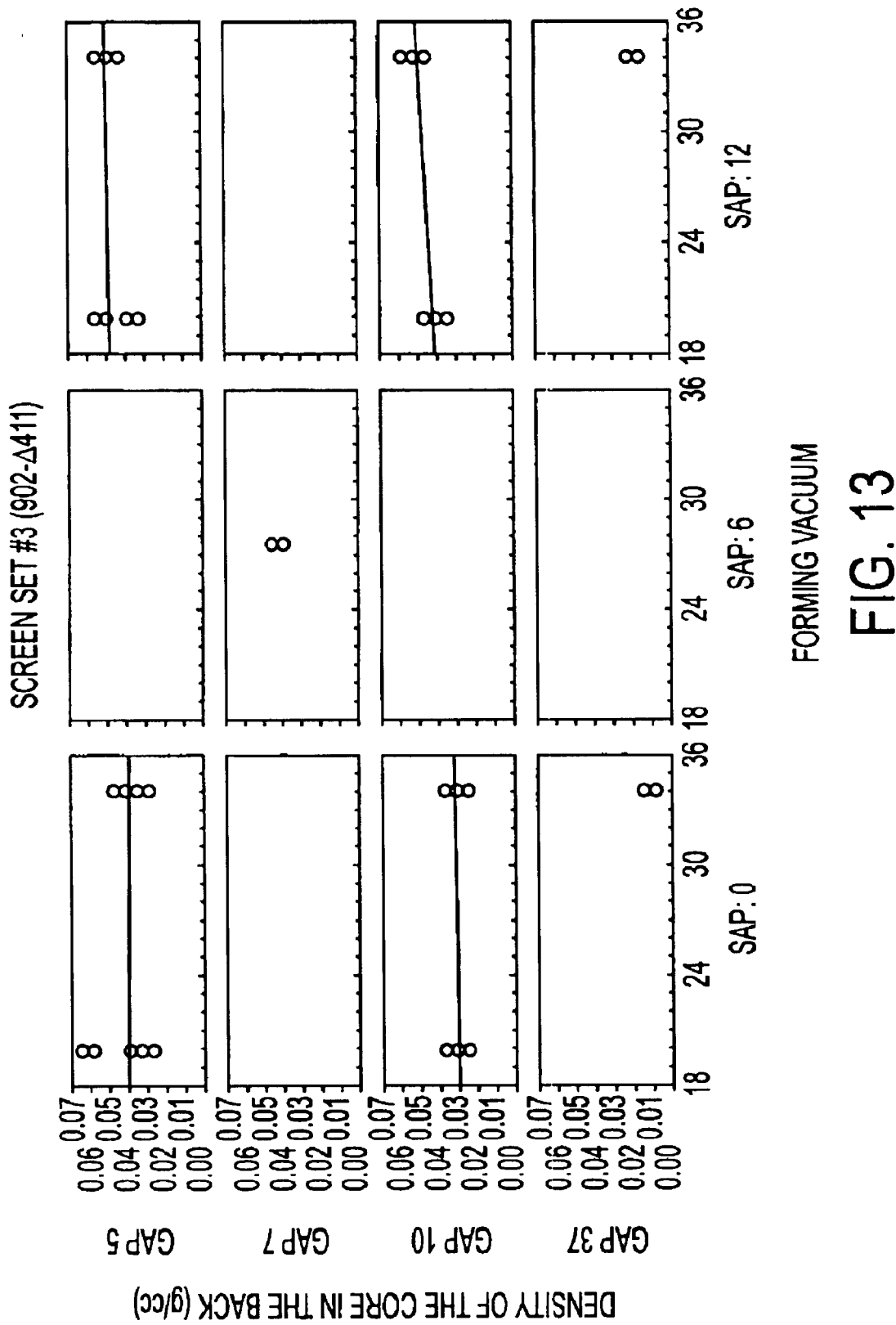
FIG. 13 is a graph illustrating the relationship between the forming vacuum and the density of the back zone of a core formed on a forming screen having 0.036 inch opening, a front zone having 49% open area and a back zone having 15% open area, in accordance with an implementation of the present invention.
Figure 14:
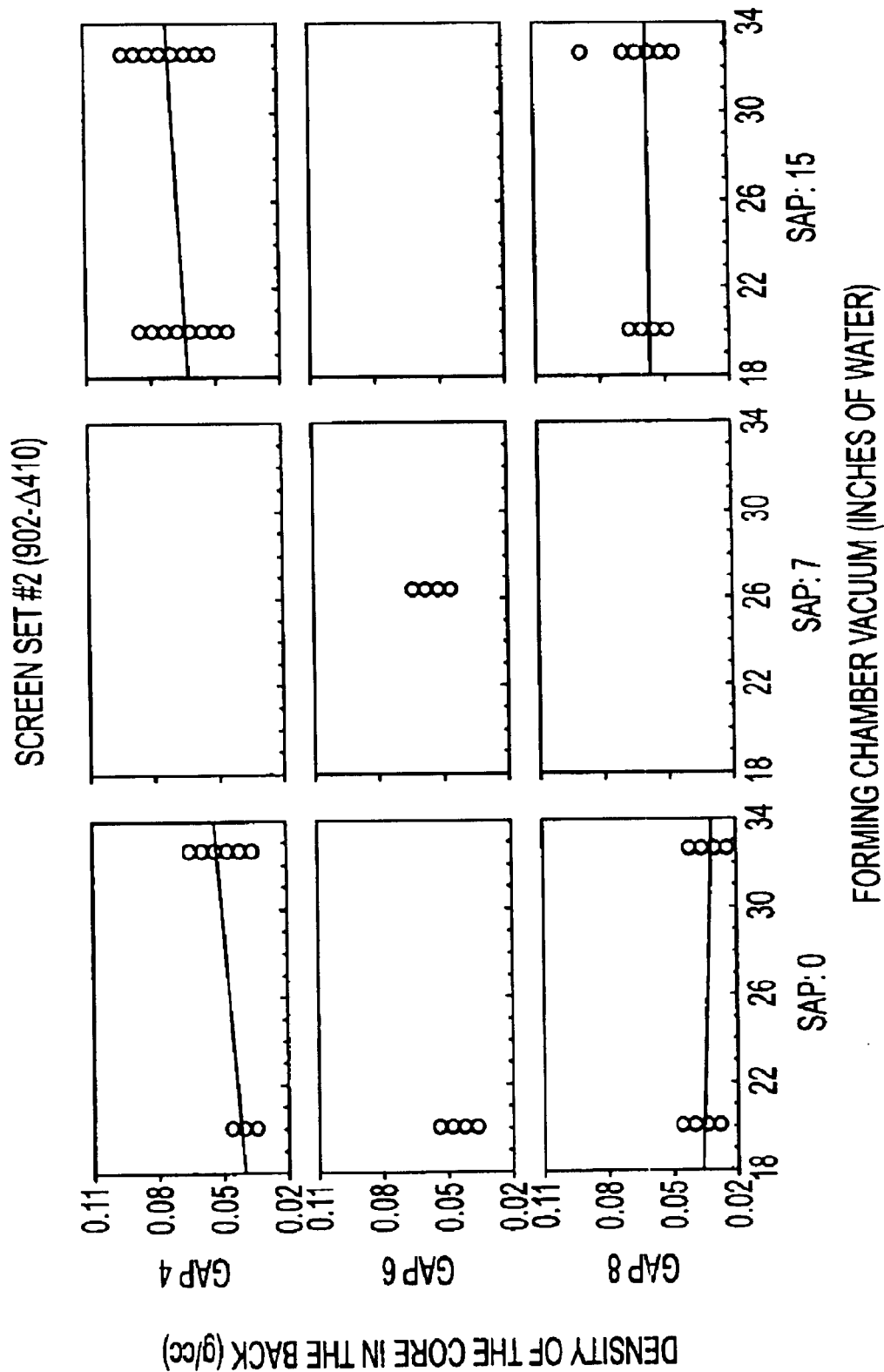
FIG. 14 is a graph illustrating the relationship between the forming vacuum and the density of the back zone of a core formed on a forming screen having 0.040 inch openings, a front zone having 49% open area and a back zone having 20% open area, in accordance with an implementation of the present invention.
Figure 15:
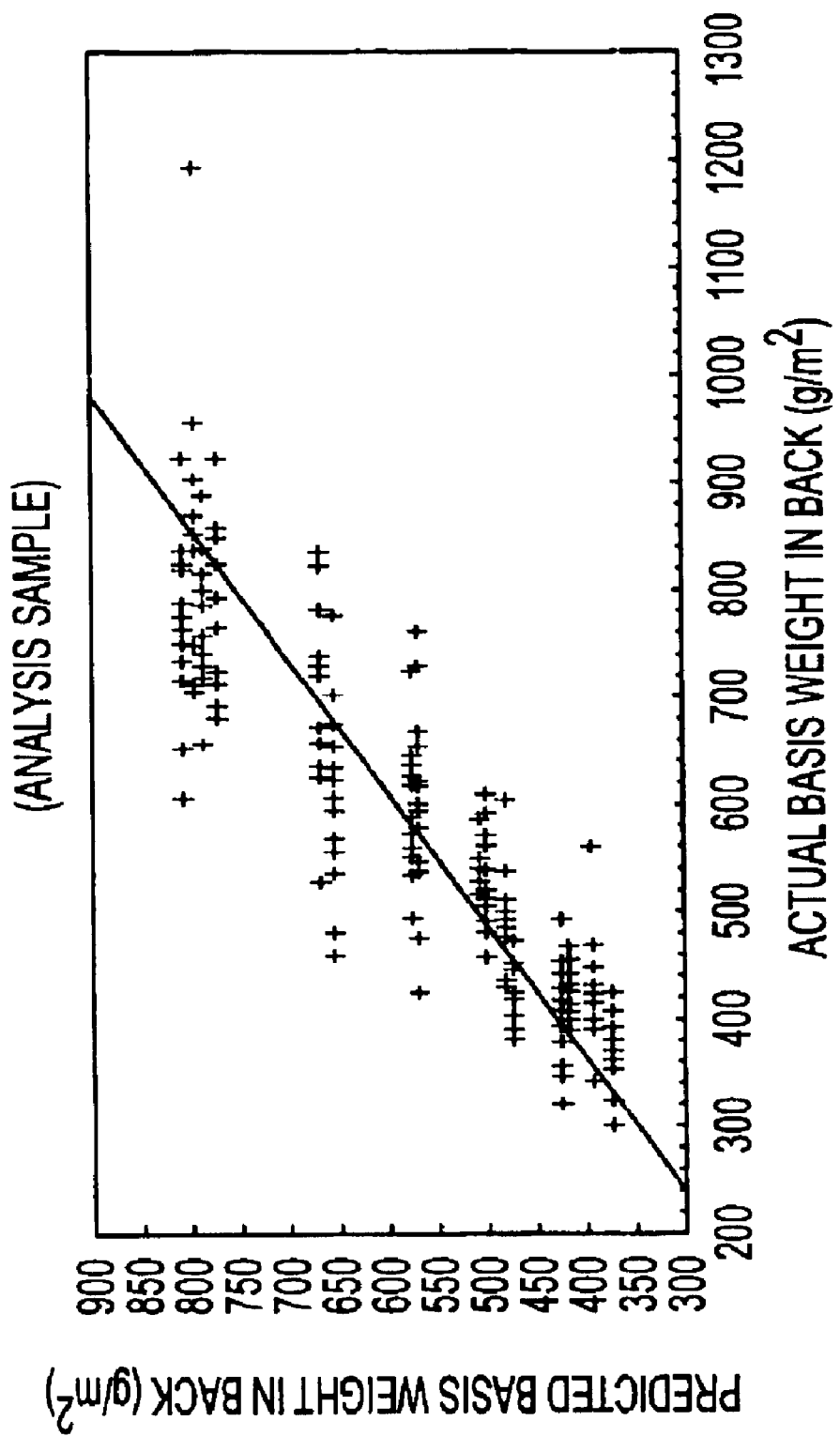
FIG. 15 is a graph illustrating the relationship between the predicted and actual Basis Weight (BW) in the back zone of a core formed on a forming screen having 0.040 inch openings, a front zone having 49% open area and a back zone having 20% open area, in accordance with an implementation of the present invention.
Figure 16:
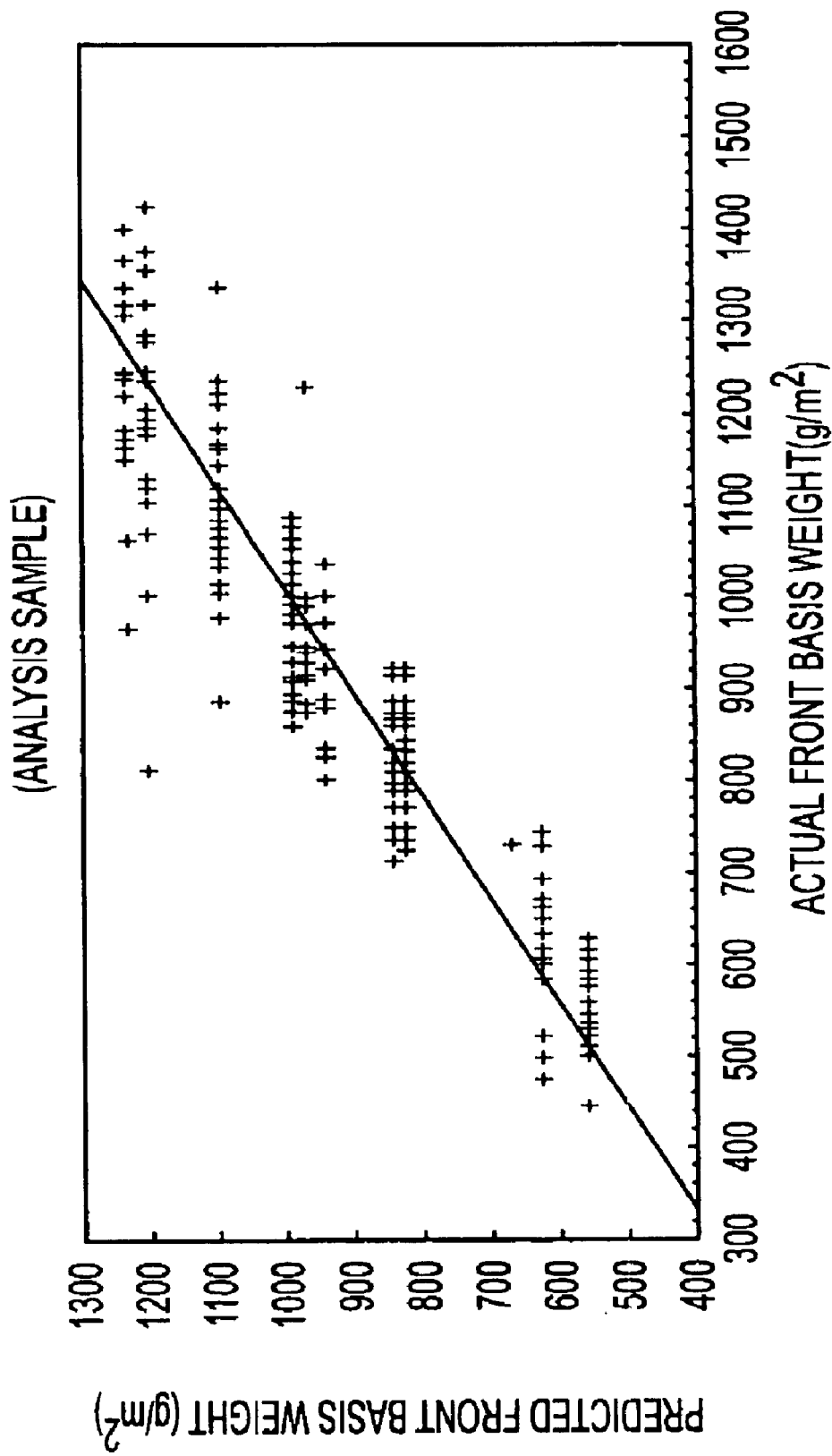
FIG. 16 is a graph illustrating the relationship between the predicted and actual Basis Weight (BW) in the front zone of a core formed on a forming screen having 0.040 inch openings, a front zone having 49% open area and a back zone having 20% open area, in accordance with an implementation of the present invention.
Figure 17:
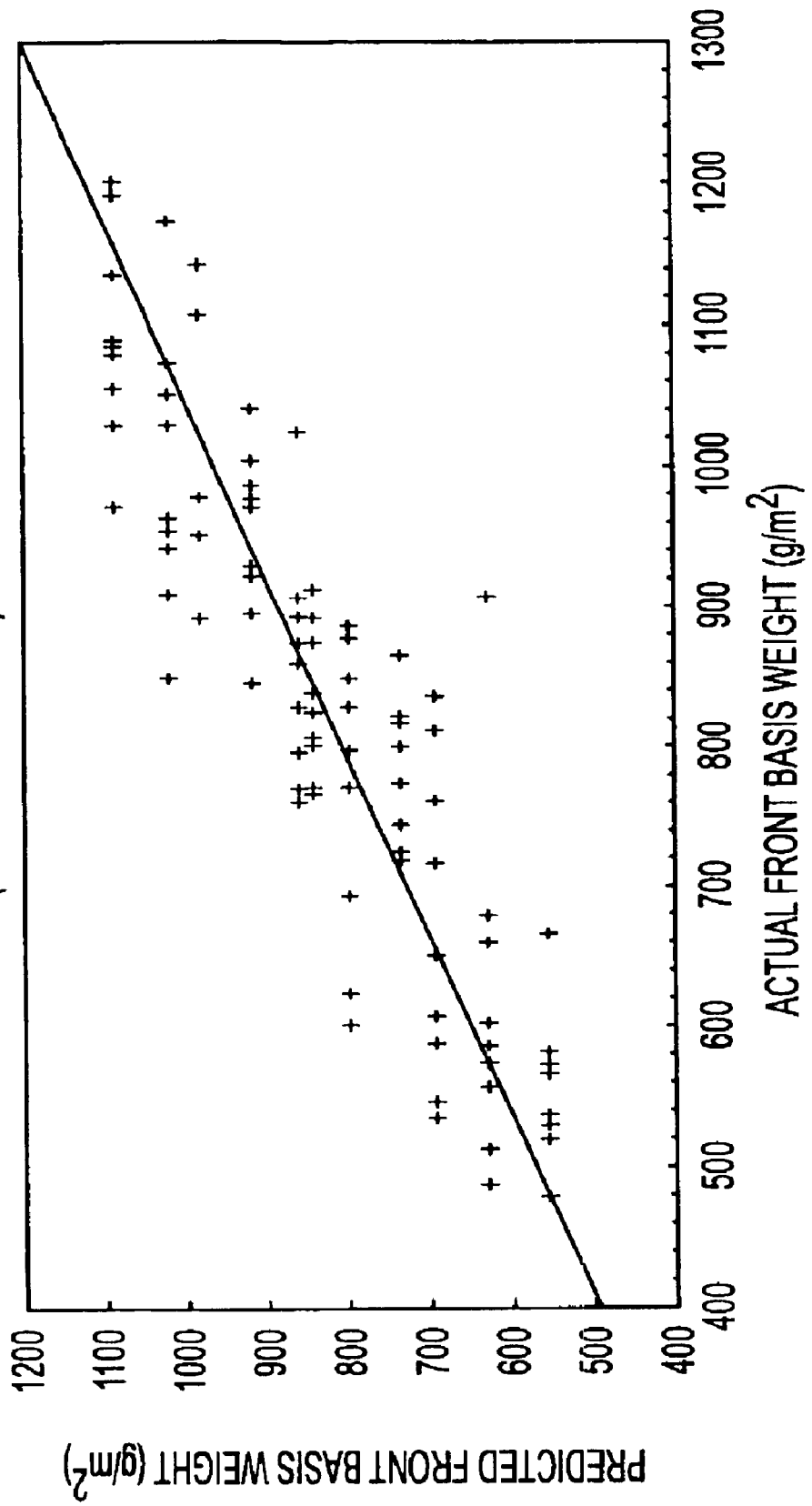
FIG. 17 is a graph illustrating the relationship between the predicted and actual Basis Weight (BW) in the back zone of a core formed on a forming screen having 0.036 inch opening, a front zone having 49% open area and a back zone having 15% open area, in accordance with an implementation of the present invention.
Figure 18:
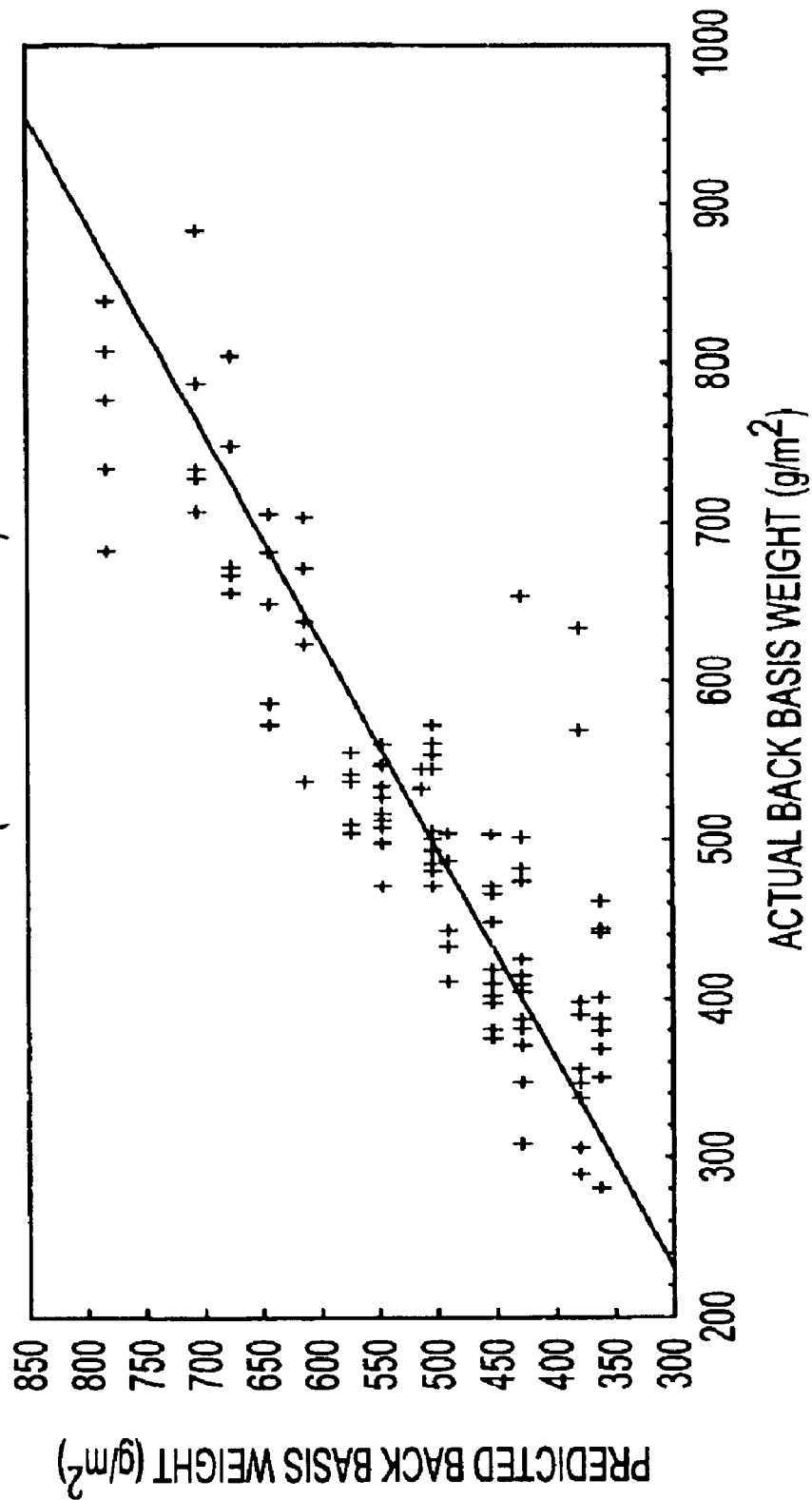
FIG. 18 is a graph illustrating the relationship between the predicted and actual Basis Weight (BW) in the front zone of a core formed on a forming screen having 0.036 inch opening, a front zone having 49% open area and a back zone having 15% open area, in accordance with an implementation of the present invention.

FIG. 8 is a plan view of an absorbent article prepared in accordance with a preferred embodiment of the present invention. Referring to FIG. 8, the absorbent article 200 is composed of a front zone 202 and a back zone 204. The absorbent article 200 is shown as one component of a disposable absorbent garment 300 according to one preferred embodiment of the present invention.

Due to the wide variety of materials which may be incorporated into the absorbent articles of the present invention, the invention is not intended to be limited to any specific materials. The particles may contain one or more fibers, one or more polymers or combinations thereof. Non-limiting exemplary fibers which may be used in the process of the present invention include, without limitation, cellulose fibers, cellulose acetate fibers, rayon fibers, Courtauld's LYOCEL fibers, polyacrylonitrile fibers, surface modified (hydrophilic) polyester fibers, surface modified polyolophin/polyester by component fibers, surface modified polyester/polyester bicomponent fibers, cotton fibers or blends thereof. Preferably cellulose acetate, rayon, Courtauld's LYOCEL, polyacrylonitrile, cotton fibers and cotton linters or combinations thereof are used in the process of the present invention. More preferably, cellulose fibers are used as the fiber material in the present invention. Other materials may be added to the fiber or pulp material which is processed in a fiberizing apparatus, such as a hammermill. The additives may be added at any point in the process. Preferably, the additives are sprayed or injected into the airborne fibers prior to the depositing of the fibers on the forming surface 2. Non-limiting exemplary additives which may be incorporated into the process of the present invention include a polymer such as a super absorbent polymer (SAP), hydrophilic polymers, potato starch, corn starch, wheat starch or rice starch, or combinations thereof. Various different combinations of materials may be used as are known to persons of ordinary skill in the art and which are described in U.S. Pat. No. 6,068,620 which is herein incorporated by reference. Preferably, the mixtures incorporated in the invention are substantially homogenous mixtures or uniformly distributed mixtures.

Although the invention preferably uses a hammermill, the invention contemplates use of any conventional fiberizing apparatus which accomplishes the disintegration of the fiber board into discreet particles of fiber. Such conventional means are well known and readily available to persons of ordinary skill in the art.

Referring again to FIG. 8, the absorbent article of the present invention has one or more predetermined zones of a specified absorbency wherein at least two of these zones have a different absorbency. Preferably, the ratio of the front absorbency to the back absorbency as measured by AUL or FVAUL, is about 1.25:1 to about 5:1, more preferably the ratio of the absorbency of the front zone to the absorbency of the back zone is about 1.5:1 to about 2.5:1, and even more preferably the ratio is about 2:1. Alternatively, the weight ratio of the basis weight of the front zone to the basis weight of the second zone is about 1.5:1 to about 3:1; more preferably, that ratio is about 1.6:1 to about 2.5:1; and most preferably, that ratio is about 2:1.

The absorbent article optionally has a third and a fourth predetermined area. Each of the third and fourth predetermined areas has a gradually increasing or decreasing absorbency or basis weight in a longitudinal direction. This gradually increasing or decreasing absorbency, as measured in AUL or FVAUL, or basis weight may be in the form of a gradual linear progression or a gradual curved progression, as desired. An absorbent article having such an absorbent profile may be prepared in accordance with the process of the present invention or any other process which achieves these same results.

The absorbent article may be composed of any material which achieves the desired absorbency. Preferably, the absorbent article contains 50 to 95% by weight particulate or fibrous sap, and about 5% to about 50% by weight of one other fibrous or particulate material. Preferably, the absorbent article comprises a laminate. For example, without limitation, the laminate can be formed by sandwiching the absorbent article between two tissue layers of laminated material to encase the absorbent article therein.

The use of AUL as a measurement of absorbency is well known in the art. A person of ordinary skill in the art would readily understand how to use AUL as a measurement of absorbency, as described herein.

FVAUL is measured in the following manner:

Finite Volume Absorbency Under Load Method (FVAUL)

Figure 19:
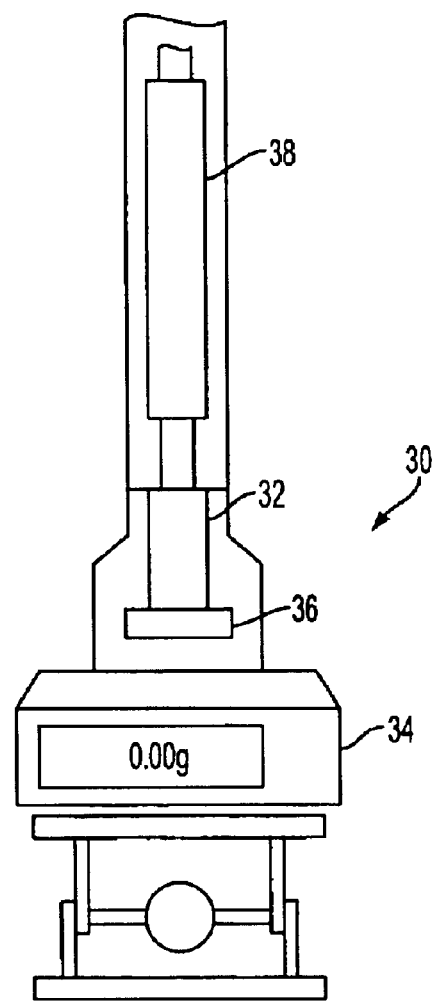
FIG. 19 is a diagrammatic view of an apparatus used to measure FVAUL in accordance with an implementation of the present invention.
Figure 20:
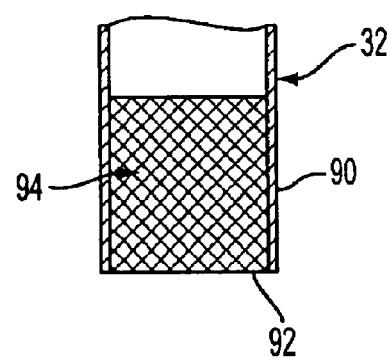
FIG. 20 is a close-up view of the weight used in the method to measure FVAUL in accordance with an implementation of the present invention.

FIG. 19 shows an apparatus used to measure finite volume absorbency under load (FVAUL), while FIG. 20 shows a close up view of a weight 32 used in the FVAUL testing. The apparatus includes balance 34 and a sample holder 36 positioned on the balance, with the weight 32 configured for positioning on a test sample held by the sample holder. An LVDT (linear variable differential transducer) measuring system 38 is positioned to engage the weight 32 and measure its movement as a finite volume of liquid is introduced into the sample holder for absorption by a test sample. A Lucas Schaevitz Type 2000 HPA LVDT system was employed, which employed Lucas Schaevitz System 96 software. Since this software only provides LVDT measurements, additional software was provided to obtain readouts of values from balance 34, and of time.

As shown in FIG. 20, the weight 32 includes a stainless steel tube 90 and a bottom stainless steel screen 92, with stainless steel slot 94 held within the tube and screen. Liquid to be introduced into a test sample is poured through the steel slot so that it passes through the screen 92 into the sample holder 36.

A computer software program that can run the LVDT (linear variable differential transducer) system was booted.

The computer program that reads information from the LVDT system and the balance calculates the free volume for the dry sample and records that as the first record in the computer file. The calculation is based on three pieces of information: the sample weight, the ratio of superabsorbent to sample weight, and the sample thickness. The samples are all assumed to be two inches in diameter. The following equation shows how the calculation is done.

$$A_s = (2 \cdot 2.54.2)^2 \cdot \pi = 10.168 \text{ cm}^2$$
$$V_s = A_s \cdot T_s$$
$$FV_s = V_s - V_{sap} - V_{pulp}$$
$$V_{sap} = M_{sap}/\rho_{sap}$$
$$V_{pulp} = M_{pulp}/\rho_{pulp}$$
$$M_{sap} = R \cdot W \quad\quad M_{pulp} = (1-R) \cdot W$$

$V_s$ = Volume of the Sample (cm$^3$)
$A_s$ = Area of the Sample (cm$^2$)
$FV_s$ = Free Volume of the Sample (cm$^3$)
$V_{sap}$ = Volume of SAP in the Sample (cm$^3$)
$V_{pulp}$ = Volume of Pulp in the sample (cm$^3$)
$\rho_{sap}$ = Density of the SAP (g/(cm$^3$)
$\rho_{pulp}$ = Density of the pulp (g/(cm$^3$)
W = The mass of the Sample (g)
R = The ration of SAP to Sample Weight (g/g)
$T_s$ = The thickness of the Sample (cm)

The LVDT system was calibrated, and the computer program to run the test was booted. 300 data sets were taken at two second intervals. A data set consists of time to the nearest hundredth second, balance reading to the nearest hundredth gram, and the LVDT reading to the nearest hundredth inch. The sample holder and a 0.16 psi porous weight were cleaned and then the holder was placed on a balance and the weight was put into place. The LVDT rods were then placed on the weights and the LVDT was zeroed.

The LVDT and the weight were removed and weighed and then the sample was placed into the holder (baby side up). The weight and LVDT were replaced and the computer program calculated the sample's thickness. The computer program asked for the sample weight and the ratio of superabsorbent particles (SAP) to sample weight. This information was used to determine the total volume being taken up by the SAP and pulp in the sample. The densities of 1.5 for SAP and 1.7 for pulp are used by the program. The computer the "calculates the free volume of the sample when dry. (If this value is known to be incorrect because of pad construction, it is possible to re-enter the free volume.)

An air shield was placed around the sample tester and the balance was zeroed (tared). 15 ml of test solution of 1 percent sodium chloride in water was prepared and placed in a graduated cylinder. The computer was then activated to start taking data sets and was allowed to take two data points before the solution was added. These two data sets are used to calculate the initial volume of the sample in the dry state. The 15 ml solution was quickly poured into the weight and was absorbed through the screen in the bottom of the weight into the sample. After the computer had taken 300 data sets, the computer generates the desired data such as dry free volume (the amount of air in the sample), the sample volume and sample mass as a function of time. The volume of the parts of the sample is calculated by taking the dry sample volume and subtracting the free volume from it and then adding the volume of liquid added.

Volume parts=(Vd−Vf )+L/1.01

Vd=Volume of Dry sample

Vf=free volume of air

L=weight of the liquid 1.01=density of 1% NaCl solution

The sample volume and the volume by parts at 60 seconds and at 600 seconds was recorded.

The following is the complete equation. 1.5 g/cc is used for the density of the superabsorbent 1.7 g/cc is used for the density of the pulp.

$$FVs = 20.268°Ts - [R°/\rho sap] - [(1-R)°W/\rho pulp]$$

The following examples are illustrative of preferred embodiments of the inventive subject matter and are not to be construed as limiting the inventive subject matter thereto.

EXAMPLES

Example 1

The following table shows the parameters for the design of forming screens used in accordance with various preferred embodiments of the present invention. The forming screens having the parameters described below are made of a sheet metal material. The arrangement of the zones is as shown in FIG. 2A and the overall configuration of the forming screens is as shown in FIG. 2B.

TABLE II

|  | T1 Zone* | Front Zone | T2 Zone* | Back Zone |
|---|---|---|---|---|
| % open area | about 5% to about 79% | about 30% to about 79% | about 5% to about 79% | about 5% to about 50% |
| Hole diameter (inches) | about 0.125 to about 0.010 | about 0.125 to about 0.010 | about 0.125 to about 0.010 | about 0.125 to about 0.010 |
| Holes per square inch | about 4 to about 10,000 | about 24 to about 10,000 | about 4 to about 10,000 | about 4 to about 6,300 |
| Thickness (inches) | about 0.005–0.250 | about 0.005–0.250 | about 0.005–0.250 | about 0.005–0.250 |

*Indicates a non-uniform transitional zone which gradually increases or decreases in open area in the longitudinal direction. This gradual increase or decrease in open area may be accomplish by increasing/decreasing hole diameter, increasing/decreasing number of holes or a combination thereof.

Example II

The following table shows the parameters for the design of a forming screen used in accordance with a preferred embodiment of the present invention. The forming screen having the parameters described below is made of a sheet metal material. The arrangement of the zones is as shown in FIG. 2A and the overall configuration of the forming screens is as shown in FIG. 2B.

TABLE III

|  | T1 Zone* | Front Zone | T2 Zone* | Back Zone |
|---|---|---|---|---|
| % open area | about 32% | about 49% | about 32% | about 15% |
| Hole diameter (inches) | about 0.036 | about 0.036 | about 0.036 | about 0.036 |
| Holes per square inch | about 481 gradually decreasing to about 147 directionally from front zone to back zone | about 481 | about 147 gradually increasing to about 481 directionally from back zone to front zone | about 147 |
| Thickness (inches) | about 0.015 | about 0.015 | about 0.015 | about 0.015 |

*Indicates a non-uniform transitional zone which gradually increases or decreases in open area in the longitudinal direction. This gradual increase or decrease in open area may be accomplish by increasing/decreasing hole diameter, increasing/decreasing number of holes or a combination thereof.

The invention has been described in connection with the preferred embodiments. These embodiments, however, are merely for example and the invention is not restricted thereto. It will be understood by those skilled in the art that other variations and modifications can easily be made within the scope of the invention as defined by the appended claims.

What is claimed is:

1. An apparatus for preparing an absorbent article, which comprises:
   a forming surface having a first predetermined zone with a first air permeability and a second predetermined zone with a second air permeability, said first air permeability being different from said second air permeability;
   a third predetermined area with a third air permeability, the third air permeability gradually increasing or decreasing from about the first air permeability to about the second air permeability along a longitudinal axis of said third predetermined area;
   means for placing particles into an airflow;
   means for guiding the airflow containing said particles through the forming surface to deposit the particles on said forming surface; and
   a drum assembly on which the forming surface is mounted.

2. The apparatus of claim 1, wherein the forming surface comprises a forming screen.

3. The apparatus of claim 1, wherein the drum assembly comprises a rotating drum.

4. The apparatus of claim 3, wherein the rotating drum comprises vacuum means for securing the particles to the forming surface.

5. The apparatus of claim 1, further comprising a hammermill positioned in a sufficient proximity to the airflow to provide particles to said airflow.

6. The apparatus of claim 1, further comprising scarfing means positioned to contact or partially contact the forming surface.

7. The apparatus of claim 1, further comprising a forming chamber which guides the airflow containing the particles to the forming surface to deposit said particles on said forming surface.

8. The apparatus of claim 1, further comprising means for generating an airflow through the forming chamber and through the forming surface.

9. The apparatus of claim 8, further comprising means for placing an additive into the airflow containing the particles as said air flow passes through the forming chamber.

10. The apparatus of claim 9, wherein the means for placing an additive into the airflow containing the particles is a means for placing a super absorbent polymer (SAP) into the airflow containing the particles.

11. An apparatus for preparing an absorbent article, which comprises:
    a forming surface having a first predetermined zone with a first air permeability and a second predetermined zone with a second air permeability, said first air permeability being different from said second air permeability;
    means for placing particles into an airflow; and
    means for guiding the airflow containing said particles through the forming surface to deposit the particles on said forming surface;
    wherein the first predetermined zone has a plurality of perforations defining an open area of about 30% to about 85% of the total area of the first predetermined zone; and the second predetermined zone has a plurality of perforations defining an open area of about 5% to about 25% of the total area of the second predetermined zone.

12. The apparatus of claim 11, wherein the first predetermined zone has a plurality of perforations defining an open area of about 40% to about 60% of the total area of the first predetermined zone; and the second predetermined zone has a plurality of perforations defining an open area of about 10% to about 22% of the total area of the second predetermined zone.

13. The apparatus of claim 11, wherein the first predetermined zone has a plurality of perforations defining an open area of about 45% to about 55% of the total area of the first predetermined zone; and the second predetermined zone has a plurality of perforations defining an open area of about 15% to about 20% of the total area of the second predetermined zone.

14. The apparatus of claim 11, wherein the forming surface comprises a forming screen.

15. The apparatus of claim 11, wherein the forming screen is a sheet metal forming screen.

16. The apparatus of claim 11, further comprising a third predetermined area with a third air permeability, the third air permeability gradually increasing or decreasing along a longitudinal axis of said third predetermined area.

17. The apparatus of claim 11, further comprising a third predetermined area with a third air permeability and a fourth predetermined area with a fourth permeability, each air permeability gradually increasing or decreasing along a longitudinal axis of each of said third and fourth predetermined areas.

18. An apparatus for preparing an absorbent article, which comprises:
    a forming surface having a first predetermined zone with a first air permeability and a second predetermined zone with a second air permeability, said first air permeability being different from said second air permeability;
    means for placing particles into an airflow;
    means for guiding the airflow containing said particles through the forming surface to deposit the particles on said forming surface; and
    a third predetermined area with a third air permeability and a fourth predetermined area with a fourth permeability, each air permeability gradually increasing or decreasing along a longitudinal axis of each of said third and fourth predetermined areas:

wherein the third air permeability or the fourth air permeability gradually increases or decreases from about the first air permeability to about the second air permeability along the longitudinal axis of each of said third and fourth predetermined areas.

19. The apparatus of claim 18, wherein the gradual increase or decrease is characterized as a linear progression.

20. The apparatus of claim 18, wherein the gradual increase or decrease is characterized as a curved progression.

21. An apparatus for preparing an absorbent article, which comprises:

a forming surface having a first predetermined zone and a second predetermined zone, said first predetermined zone having a first plurality of openings defining an area of about 30% to about 85% of the total area of the first predetermined zone, said second predetermined zone having a second plurality of openings defining an area of about 5% to about 25% of the total area of the second predetermined zone;

a rotating drum on which the forming surface is mounted;

means for placing particles into an airflow; and means for guiding the airflow through a forming chamber and the forming surface to deposit the particles on the forming surface.

22. The apparatus of claim 21, wherein the rotating drum comprises vacuum means for securing the particles to the forming surface.

23. The apparatus of claim 21, further comprising a hammermill positioned in sufficient proximity to the airflow to generate the airborne particles.

24. The apparatus of claim 21, further comprising scarfing means positioned to contact or partially contact the forming surface.

25. The apparatus of claim 21, further comprising means for providing an additive into the airflow containing the particles as the airflow passes through the forming chamber.

26. The apparatus of claim 25, wherein the means for placing an additive into the airflow containing the particles is a means for placing a super absorbent polymer (SAP) into the airflow containing the particles.

27. The apparatus of claim 21, wherein the first plurality of openings defines an area of about 40% to about 60% of the total area of the first predetermined zone; and the second plurality of openings defines an area of about 10% to about 22% of the total area of the second predetermined zone.

28. The apparatus of claim 21, wherein the first plurality of openings defines an area of about 45% to about 55% of the total area of the first predetermined zone; and the second plurality of openings defines an area of about 15% to about 20% of the total area of the second predetermined zone.

29. The apparatus of claim 21, wherein the forming surface comprises a forming screen.

30. The apparatus of claim 29, wherein the forming screen is a sheet metal forming screen.

31. The apparatus of claim 21, wherein the size of each opening is uniform in size with every other opening on the forming surface.

32. The apparatus of claim 21, wherein the diameter of each opening in the forming surface ranges from about 0.030 inches to about 0.050 inches.

33. The apparatus of claim 21, wherein the diameter of each opening in the forming surface ranges from about 0.036 inches to about 0.040 inches.

34. The apparatus of claim 33, wherein the first predetermined zone has about 24 openings per square inch to about 10,100 openings per square inch.

35. The apparatus of claim 33, wherein the second predetermined zone has about 4 openings per square inch to about 6,300 openings per square inch.

36. The apparatus of claim 21, further comprising a third predetermined zone having a third plurality of openings defining a gradually increasing or decreasing area along a longitudinal axis of the third predetermined zone.

37. The apparatus of claim 21, further comprising a fourth predetermined zone having a fourth plurality of openings defining a gradually increasing or decreasing area along a longitudinal axis of the fourth predetermined zone.

38. An apparatus for preparing an absorbent article, which comprises:

a forming surface having a first predetermined zone with a first air permeability and a second predetermined zone with a second air permeability, said first air permeability being different from said second air permeability;

a third predetermined area with a third air permeability, the third air permeability gradually increasing or decreasing from about the first air permeability to about the second air permeability along a longitudinal axis of said third predetermined area;

means for placing particles into an airflow;

means for guiding the airflow containing said particles through the forming surface to deposit the particles on said forming surface; and scarfing means positioned to contact or partially contact the forming surface.

* * * * *